US012708630B2

(12) United States Patent
Jung et al.

(10) Patent No.: US 12,708,630 B2
(45) Date of Patent: Aug. 18, 2026

(54) COMBINED THERAPY OF 4'-THIO-5-AZA-2'-DEOXYCYTIDINE AND VENETOCLAX

(71) Applicant: PINOTBIO, INC., Suwon-si (KR)

(72) Inventors: Doo-young Jung, Suwon-si (KR); Jin-soo Lee, Suwon-si (KR); Hyun-yong Cho, Suwon-si (KR); Young-hwa Chun, Suwon-si (KR)

(73) Assignee: PINOTBIO, Inc., Suwon-si (KR)

( * ) Notice: Subject to any disclaimer, the term of this patent is extended or adjusted under 35 U.S.C. 154(b) by 389 days.

(21) Appl. No.: 18/285,751

(22) PCT Filed: Apr. 5, 2022

(86) PCT No.: PCT/KR2022/004846
§ 371 (c)(1),
(2) Date: Oct. 5, 2023

(87) PCT Pub. No.: WO2022/215995
PCT Pub. Date: Oct. 13, 2022

(65) Prior Publication Data

US 2025/0281510 A1 Sep. 11, 2025

(30) Foreign Application Priority Data

Apr. 5, 2021 (KR) ........................ 10-2021-0044289
Aug. 2, 2021 (KR) ........................ 10-2021-0101179

(51) Int. Cl.

| | |
|---|---|
| ***A61K 31/635*** | (2006.01) |
| ***A61K 31/53*** | (2006.01) |
| ***A61K 31/706*** | (2006.01) |
| ***A61P 35/00*** | (2006.01) |
| ***A61P 35/02*** | (2006.01) |

(52) U.S. Cl.
CPC ............ *A61K 31/635* (2013.01); *A61K 31/53* (2013.01); *A61P 35/00* (2018.01); *A61P 35/02* (2018.01)

(58) Field of Classification Search
CPC ..... A61K 31/635; A61K 31/706; A61P 35/00; A61P 35/02
See application file for complete search history.

(56) References Cited

FOREIGN PATENT DOCUMENTS

| | | | |
|---|---|---|---|
| JP | 2018-537450 | A | 12/2018 |
| KR | 10-2007-0107576 | A | 11/2007 |
| KR | 10-2017-0104616 | A | 9/2017 |
| KR | 10-1813830 | B1 | 12/2017 |
| KR | 10-2019-0032295 | A | 3/2019 |

OTHER PUBLICATIONS

Mehdipour et al., "The role of DNA-demethylating agents in cancer therapy", Pharmacology & Therapeutics, vol. 205, No. 107416, 2020, pp. 1-14.
Monge et al., "Trial in progress abstract phase I trial of 5-aza-4'-thio-2'-deoxycytidine (Aza-TdC) in patients with advanced solid tumors.", Journal of Clinical Oncology, vol. 37, No. 15, 2019 ASCO Annual Meeting I, Meeting Abstract, 2019 (2 pages total).
Extended European Search Report issued Mar. 12, 2025 in Application No. 22784904.9.
Courtney D Dinardo, et al., "Venetoclax combined with decitabine or azacitidine in treatment-naive, elderly patients with acute myeloid leukemia", blood, Jan. 3, 2019, vol. 133, No. 1, pp. 7-17 (11 pages).
Jaideep V. Thottassery, et al. "Novel DNA methyltransferase-1 (DNMT1) depleting anticancer nucleosides, 4'-thio-2'-deoxycytidine and 5-aza-4'-thio-2'-deoxycytidine", Cancer Chemother Pharmacol, 2014, vol. 74, pp. 291-302 (12 pages).
Korean Office Action dated Mar. 26, 2024 in Application No. 10-2022-0042113.
International Search Report for PCT/KR2022/004846 dated Jul. 12, 2022.

*Primary Examiner* — Bruck Kifle
(74) *Attorney, Agent, or Firm* — Sughrue Mion, PLLC

(57) ABSTRACT

The present invention relates to the combination therapy of 4'-thio-5-aza-2'-deoxycytidine (Aza-T-dCyd), a multi-target inhibitor including a DNMT1 inhibitor, and Venetoclax, an inhibitor of BCL-2, which mediates apoptosis.

15 Claims, 30 Drawing Sheets

DNA methylation
• Blocked access of RNA synthetase
• Suppression of gene expression
DNA methylation
• Structural changes in histones
Normal, unmethylated DNA
• Normal expression of genes
DNA methylation
• Structural changes in chromosomes
Chromosome
Histone
M: methylation Nature Reviews Immunology, vol. 7, p. 105 (2007)

Decitabine

Azacytidine

NbA
NsA
Extracellular
NsA
NsA
Fluoropyrimidines
NsA
Clofarabine, Fludarabine, Cladribine, Gemcitabine
Thiopurines Fluoropyrimidines
RNA incorporation
NsA
Cytarabine, Clofarabine, Cladribine, Nelarabine, Gemcitabine
(Chain elongation)
DNA incorporation
Futile repair
Thiopurines Fluoropyrimidines
DNA lesion
Decitabine, Azacitidine, Zebularine Regulation of apoptosis by the BCL-2 family.

https://www.nature.com/articles/cdd201782#Abs1

| Treatment | Expr. Ratio | Std. Error | 95% Confidence | P Value | Result |
|---|---|---|---|---|---|
| NTX-301_6nM | 1.292 | 1.073 - 1.664 | 0.834 - 1.833 | 0.1175 | NoDifference |
| NTX-301_20nM | 1.548 | 1.228 - 1.929 | 1.039 - 2.342 | 0.0455 | Up |
| NTX-301_60nM | 2.269 | 1.641 - 3.185 | 1.263 - 3.670 | 0.0170 | Up |
| NTX-301_200nM | 4.768 | 3.825 - 5.948 | 3.459 - 6.577 | 0.0350 | Up |

| Cell line | MV4-11 | THP-1 | HL-60 | OCI-AML-3 |
|---|---|---|---|---|
| NTX-301 $IC_{50}$ (μM) | 0.19 | 0.69 | 0.15 | 0.014 |

| Comparison of Growth Inhibitory Effects of NTX-301 and Decitabine on Hematologic Cancer Cell Lines | | |
|---|---|---|
| **Cell line** | **$GI_{50}$ (μM)** | |
| | **Decitabine** | **Aza-T-dCyd** |
| MV4-11 | 0.75 | 0.19 |
| THP-1 | 4.3 | 0.69 |
| HL-60 | 4.0 | 0.15 |
| OCI-AML-3 | 0.29 | 0.014 |
| Jurkat | 0.024 | 0.018 |
| KG-1 | 0.045 | 0.077 |

❖ Drug efficacy & DNA replication

❖ Drug efficacy & replication stress-related features

COMBINED THERAPY OF 4'-THIO-5-AZA-2'-DEOXYCYTIDINE AND VENETOCLAX

CROSS REFERENCE TO RELATED APPLICATIONS

This application is a National Stage of International Application No. PCT/KR2022/004846 filed Apr. 5, 2022, claiming priority based on Korean Patent Application No. 10-2021-0044289 filed Apr. 5, 2021 and Korean Patent Application No. 10-2021-0101179 filed Aug. 2, 2021, the entire disclosures of which are incorporated herein by reference.

TECHNICAL FIELD

The present invention relates to the combination therapy of 4'-thio-5-aza-2'-deoxycytidine (Aza-T-dCyd), a multi-target inhibitor including a DNMT1 inhibitor, and Venetoclax, an inhibitor of BCL-2, which mediates apoptosis.

BACKGROUND ART

Nucleoside derivatives are organic compounds with structures very similar to the building blocks of DNA and RNA, which perform the most essential functions of the cells that make up our body (maintaining life functions through replication/division), and have played a central role in anticancer chemotherapy/antiviral chemotherapy.

Since the 1960s, various nucleoside-based anticancer drugs such as Cytarabine, Clofarabine, Fludarabine, 5-Fluorouracil (including Capecitabine), Gemcitabine, Decitabine, Azacytidine, etc. have been commercialized (FIG. 4), and many of them are classified as major anticancer drugs that are included in the WHO's Essential Medication List.

Decitabine (also known as Dacogen® or 5-aza-2'-deoxycytidine) is a pyrimidine nucleoside analog of cytidine that induces DNA hypomethylation by inhibiting DNA methyltransferase (DNMT). Specifically, decitabine functions by incorporating into DNA strands during replication, and when a DNA methyltransferase such as DNMT1 binds to the DNA and replicates methylation on the daughter strand, the DNMT is irreversibly bound to decitabine and cannot be dissociated. Thus, decitabine action is cell division dependent. Cells that divide much faster than most other cells in the body (e.g., cancer cells) are more severely affected by decitabine. This means that decitabine is used to treat cancers such as myelodysplastic syndromes (MDS) and leukemias, including acute myeloid leukemia (AML), where DNA hypermethylation is important for development.

Existing nucleoside-based anticancer drugs act not only on cancer cells, but also on normal cells that divide rapidly, such as bone marrow/digestive tract and mucous membrane/skin cells, so there is a problem that they show side effects, (i) for Azacytidine (Vidaza), nausea, anemia, thrombocytopenia, vomiting, pyrexia, leukopenia, diarrhea, injection site erythema, constipation, neutropenia, ecchymosis, petechiae, rigors (chills), weakness (malaise), hypokalemia; and (ii) for Decitabine (Dacogen), neutropenia, thrombocytopenia, anemia, fatigue, pyrexia (fever), nausea, cough, petechiae, constipation, diarrhea, hyperglycemia, and hyperglycemia, and various resistance mechanisms occur due to limited usage, limiting the treatment effect.

Although the genes in our body have the same sequence in each cell, the cells in our body are very precisely regulated to express only certain genes in certain tissues and not others.

The mechanism by which this acquired regulation is accomplished is called epigenetic regulation, and it consists of (1) changes in DNA, (2) changes in histones, which physically bind to DNA and form the chromatin structure, and (3) changes in other components of the chromatin structure.

DNA methylation is the most fundamental epigenetic mechanism and regulates the expression of genes by methylating the C base of CpG sequence among various gene components such as gene body, promoter, and enhancer. Generally, CpG sequences are present in the promoter region, and genes with high CpG methylation in the promoter are not expressed well. Conversely, genes with less CpG methylation are actively expressed (FIG. 1).

In the body, DNA methylation is known to occur in two steps: (1) DNA methyltransferase (DNMT) 3A or 3B methylates de novo DNA during tissue differentiation and development to determine the pattern of gene expression for each tissue; and (2) DNMT1 methylates DNA by faithfully replicating the DNA methylation pattern already established by each cell in the tissue.

In a typical cell, in regions of highly methylated DNA, DNMT1 binds to other proteins, especially histone proteins and other repressor proteins that inhibit gene expression, forming structures that make it difficult for genes to be expressed. Conversely, when DNA is not heavily methylated, it creates a structure that is easier for gene expression and promotes gene expression. DNA methylation plays an important role in ensuring that each cell in the body expresses the right combination of genes to fulfill its designated function. When these functions are disrupted, it can lead to a variety of diseases.

Myelodysplastic syndromes (MDS) and acute myeloid leukemia (AML) are cancers that originate in the bone marrow, where clones that produce immature leukemia cells (leukemic blasts) overwhelm the number of clones that normally produce various blood cells, causing the blood to become filled with leukemic blasts that cannot function normally. Ultimately, the disease leads to death due to failure of blood function.

The normal process of hematopoiesis in the body consists of the following steps (1) hematopoietic stem cells are stimulated to produce blood cells; (2) hematopoietic stem cells divide rapidly in phase 1 to differentiate into progenitor cells that can produce a sufficient number of blood cells; (3) after the progenitor cells divide and have a sufficient number of progenitor cells; (4) they undergo phase 2, in which they stop dividing/multiplying and each has its own function; and (5) they mature into functional cells that no longer divide (FIG. 2).

Master transcription factors (Master TFs) play a major role in this process. When hematopoietic stem cells are stimulated in phase 1, progenitor-generating master transcription factors such as CEBP/alpha act strongly to ensure that a sufficient number of progenitor cells are generated, and then, once a sufficient number of progenitor cells are generated, they enter phase 2 and produce master TFs such as CEBP/epsilon. Phase II master TFs degrade phase I master TFs so that rapid division/proliferation no longer occurs and the cell matures along a defined pathway.

In MDS and AML, the gene promoters of the phase II Master TFs that drive this transformation process are hypermethylated for a number of reasons, resulting in decreased expression of these phase II Master TFs. This causes the progenitor cells to fail to reach maturity and continue to divide/proliferate, producing a constant stream of immature cells. As this process progresses further, multiple mutations (FLT3-ITD, etc.) accumulate, leading to rapidly progressive malignant AML, which is often fatal.

Many cases of MDS/AML are characterized by DNMT1 overactivation, resulting in abnormal methylation patterns, and conversely, inhibition of DNMT1 can normalize the epigenetic mechanisms of action, leading to a cure for these diseases (FIG. 3).

There are various causes of promoter hypermethylation of the Master TF gene, including changes in methylation patterns due to abnormalities in DNMT family enzymes (overexpression, overactivation, deletion/mutation, etc.), abnormalities in methylation patterns caused by abnormalities in the IDH1/2 enzymes that make it difficult for them to be removed, abnormalities in methylation patterns due to abnormalities in TET enzymes that make it difficult for them to be removed, and accumulation of epigenetic changes due to aging. In any case, it has been confirmed that inhibiting the activation of DNMT1, a maintenance DNA methylation machinery that keeps the methylation pattern intact in the process of growth/division/survival of cells, can resolve the hypermethylation pattern and lead to therapeutic efficacy in MDS/AML.

While the course of treatment for acute myeloid leukemia (AML), myelodysplastic syndromes (MDS), or acute lymphocytic leukemia (ALL) depends on the classification of the disease, the age and health status of the patient, and other factors, the general standard of care (SoC) is that, unlike solid tumors, which involve surgery to remove the cancerous tumor, induction therapy with chemotherapy to reduce blasts, and consolidation therapy after complete remission is achieved, maintenance therapy to keep the patient in remission. For severely ill patients who are in urgent need of treatment, hematopoietic cell transplant (HCT) may be the most effective option, but it is only possible after the patient's abnormal bone marrow has been completely removed through intense chemotherapy or radiotherapy, so it is very limited for elderly patients who are in poor physical condition.

Age itself is the most important risk factor for leukemia, especially AML and MDS, because the likelihood of genetic mutations that can cause blood cancers, or bone marrow diseases, increases significantly with aging, whereas, compared to relatively younger patients in good physical condition, elderly patients with weakened physical function due to various factors such as underlying medical conditions are often difficult to treat with conventional chemotherapy, which is highly toxic, and even if they are treated with it, their prognosis is often poor, with frequent relapses and very high rates of premature death.

Treatment of MDS/AML cells (cell lines or patient-derived samples) with the DNMT1 inhibitor Decitabine/Azacytidine reduces hypermethylation of the CEBP/epsilon promoter, a phase II master TF, resulting in the expression of CEBP/epsilon and the expression of tumor suppressor genes such as p27, a downstream effector of CEBP/epsilon, and shows anticancer effects.

Two existing commercialized DNMT1 inhibitors, Dacogen (Decitabine) and Vidaza (Azacytidine), have been used as standard of care for the treatment of MDS/AML in elderly patients, but various problems have been pointed out, such as insufficient efficacy, high toxicity, problems in convenience of use due to administration route (IV or subcutaneous injection), and expansion of DNMT1 inhibitor market through expansion of indications.

On the other hand, the majority of acute lymphocytic leukemias (ALL) are B-ALL with B-cell origin, while some are T-cell ALL (T-ALL) with T-cell origin, and the development of adequate targeted therapies for T-ALL is limited, resulting in limited treatment options after first-line chemotherapy.

For adult ALL, high-intensity chemotherapy based on cyclophosphoamide, daunorubicin, vincristine, L-asparaginase, and prednisone is the first-line treatment option.

About 30-40% of patients relapse or acquire resistance despite these high-intensity chemotherapy regimens, and among these relapsed/resistant patients, there are various treatment options such as antibody therapies, ADCs, and CAR-Ts for B-cell ALL patients, but there is a high demand for the development of new therapies for T-ALL patients, as the treatment options are limited to nelarabine.

While many patients with T-ALL respond well to intensive chemotherapy with a combination of various cytotoxic agents, there is a high need for the development of new therapies for patients with T-ALL who have developed resistance despite the use of standard therapies. In some of these resistant patients, it has been identified that resistance is caused by overexpression of anti-apoptotic genes such as BCL-2, and treatment with DNMT1 inhibitors (such as Decitabine) and Venetoclax has been tried, and excellent therapeutic synergy has been confirmed.

However, as existing nucleoside-based anticancer drugs are applied to the treatment of T-cell ALL, nucleoside metabolic resistance is likely to occur in resistant patients, and there is a high need to develop new DNMT1 inhibitors that can overcome various resistance mechanisms including metabolic resistance beyond the existing Decitabine.

There are a number of drugs on the market based on the DNMT1 inhibitor active ingredients Decitabine and Azacytidine (injectable, oral, utilized for each application).

Both decitabine and azacytidine, whose chemical structures are shown in FIG. 4, are activated in the cell as decitabine triphosphate and incorporated into DNA, which then traps the DNMT1 enzyme to form a DNA-DNMT1 covalent adduct. It has a mechanism of removing hypermethylation and showing various anti-cancer effects by various intracellular signal transduction pathways that occur during DNA damage repair through the decomposition of the generated adduct, but (1) Both Decitabine/Azacytidine are vulnerable to metabolism by Cytidine Deaminase in the body, which limits the effectiveness due to the problem of unstable PK profile, (2) Because it damages DNA through the formation of DNA-DNMT1 adducts, it damages not only cancer cells but also normal tissues of the body such as bone marrow and gastrointestinal mucosa, so there is a limit to the anti-cancer effect as the amount of use is limited, and (3) In cancer cells that survive after initial treatment, the anti-cancer effect is suppressed due to the overactivation of the elimination process after the formation of DNA-DNMT1 adducts, showing a vulnerable appearance to the development of resistance, so the development of improved new drugs is strongly required.

In the case of Decitabine/Azacytidine, it is vulnerable to metabolism by cytidine deaminase in the body and has an unstable PK profile, which limits its effectiveness.

Based on the fact that both the 5'-OH and 3'-OH groups of the Decitabine/Azacytidine structure must be exposed for metabolism by cytidine deaminase, Astex Pharmaceuticals/Otsuka developed SGI-110, a decitabine prodrug with a deoxyguanidine linkage to the 3'-OH group of decitabine. SGI-110 was confirmed to have an improved PK profile by avoiding metabolism by cytidine deaminase and slow release of the decitabine component when administered to humans, but the limitations of this improved PK profile did not translate into improved pharmacological efficacy.

In order to solve the problem of metabolism by cytidine deaminase, improved new drugs such as an oral drug (ASTX-727) that takes a cytidine deaminase inhibitor or an oral drug (CC-486) that stabilizes the PK profile by administering excessive amounts of azacytidine have been developed, but they do not provide a solution to the problems (2) and (3) of Decitabine/Azacytidine described above. In addition, there are problems such as decreased efficacy of the active ingredient (Decitabine) due to the combination of cytidine deaminase inhibitors and gastrointestinal side effects due to excessive drug administration, so it is necessary to develop new DNMT1 inhibitors that can solve these problems.

Currently, decitabine/azacytidine or a combination of these drugs with Venetoclax is the standard of care for elderly MDS/AML patients, but there are problems such as limited therapeutic response in only about 40% of patients when administered alone and only about 65% of patients when administered in combination, rapid resistance, and cross-resistance between decitabine/azacytidine drugs.

In addition, in the case of elderly MDS/AML, unlike the development of various targeted anti-cancer drugs/immunotherapy drugs/cell therapy drugs in general MDS/AML, the applicable development technologies are limited, and the applicable development technologies are limited in the fields of recurrent T-ALL, platinum-resistant ovarian cancer/bladder cancer, etc.

DETAILED DESCRIPTION OF THE INVENTION

Technical Problem

To address the aforementioned problems with DNMT1 inhibitors, the present invention seeks to provide a combination therapy of 4'-thio-5-aza-2'-deoxycytidine (Aza-T-dCyd), a multi-targeted inhibitor that includes DNMT1 inhibition, and Venetoclax, an inhibitor of BCL-2, which mediates apoptosis.

Technical Solution

A first aspect of the present invention provides a pharmaceutical composition for treating or preventing cancer comprising a 4'-thio-5-aza-2'-deoxycytidine drug and a venetoclax drug, wherein both drugs are co-administered in the same formulation or in different formulations.

A second aspect of the invention provides a pharmaceutical composition for treating or preventing cancer comprising a 4'-thio-5-aza-2'-deoxycytidine drug and a venetoclax drug, wherein both drugs are intended to be administered to a subject via the same route or different routes.

A third aspect of the invention provides a pharmaceutical composition for treating or preventing cancer comprising a 4'-thio-5-aza-2'-deoxycytidine drug and a venetoclax drug, wherein both drugs are intended to be administered to a subject by parenteral or oral administration.

A fourth aspect of the invention provides a pharmaceutical composition for treating or preventing cancer comprising a 4'-thio-5-aza-2'-deoxycytidine drug and a venetoclax drug administered simultaneously or sequentially.

A fifth aspect of the invention provides a pharmaceutical composition for treating or preventing cancer comprising a 4'-thio-5-aza-2'-deoxycytidine drug, wherein the pharmaceutical composition is administered concurrently with a venetoclax drug. A sixth aspect of the invention provides a pharmaceutical composition for treating or preventing cancer comprising a 4'-thio-5-aza-2'-deoxycytidine drug, wherein the pharmaceutical composition is administered sequentially with a venetoclax drug. A seventh aspect of the invention provides a kit comprising a 4'-thio-5-aza-2'-deoxycytidine drug and a venetoclax drug.

In any one of the first to seventh aspects, the 4'-thio-5-aza-2'-deoxycytidine drug may be administered at 8 mg/day or more and less than 32 mg/day.

In any of the first to seventh aspects, the 4'-thio-5-aza-2'-deoxycytidine drug may be administered at a dose of 75% or less of the maximum tolerable dose (MTD), preferably at a dose of 25% to 75%, more preferably at a dose of 25% to 50%.

In any one of the first to seventh aspects, the 4'-thio-5-aza-2'-deoxycytidine drug may reduce DNMT1 protein or inhibit DNMT1 in a concentration-dependent manner.

In any of the first to seventh aspects, the 4'-thio-5-aza-2'-deoxycytidine drug may be administered at a high dose that prevents the mechanism of resistance development from overactivating base excision repair (BER), one of the methods of DNA damage repair. In this case, the 4'-thio-5-aza-2'-deoxycytidine drug can overcome the mechanism of resistance by reducing the efficiency or speed of the BER (Base Excision Repair) repair process that is overactivated by the mechanism of resistance through its strong resistance to nucleic acid endonucleases.

The pharmaceutical compositions of any one of the first to sixth aspects, or the drugs in the kit of the seventh aspect, may be used to treat a patient in need thereof who has developed resistance to a DNMT1 inhibitor; who has accumulated altered epigenetic DNA methylation patterns in cancer cells relative to normal cells; who has been informed of or diagnosed with a poor prognosis or potential for resistance to DNMT1 inhibitors; who has been diagnosed with an elevated level of lineage commitment master transcription factors selected from the group consisting of CEBP/alpha, Pu.1 and GATA factors, while expression of CEBP/epsilon or late developmental stage transcription factors remains low due to hypermethylation of each gene, relative to normal individuals; who has a known or diagnosed risk of developing nucleoside metabolism resistance when receiving nucleoside-based anticancer agents; who is a candidate for platinum-based anticancer agents; who have developed or are likely to develop resistance to platinum-based anticancer agents; and/or who are epigenetically silenced for tumor suppressor genes and/or SLEN11 relative to normal individuals.

In this case, information regarding prognosis or the likelihood of developing resistance may be derived from (i) quantifying the problem of overactivation of the DNA-DNMT1 adduct formation and removal process resulting in inhibition of anticancer efficacy, or (ii) stratifying the patient population based on whether/to what extent the problem occurs. For example, the data value of providing poor prognostic information may be the likelihood of disease recurrence and/or early mortality (median survival of less than 1 year).

In any of the first to seventh aspects, the drug 4'-thio-5-aza-2'-deoxycytidine may be administered as a targeted anti-cancer agent at or above a standard dosage of a DNMT1 inhibitor to a patient in need thereof who is limited in the standard dosage of a DNMT1 inhibitor due to the fact that the DNMT1 inhibitor damages DNA through the formation of DNA-DNMT1 adducts, thereby damaging normal tissue as well as cancer cells.

The pharmaceutical composition of any one of the first to sixth aspects, may be administered to a patient population diagnosed with acute myeloid leukemia (AML), myelodysplastic syndrome (MDS), or acute lymphocytic leukemia (ALL), to a patient population with platinum-resistant recurrent end-stage ovarian cancer, or to a patient population with platinum-resistant metastatic bladder cancer, to a patient population with metastatic bladder cancer, to a patient population with p53 mutated bladder cancer or hypermethylated SLFN11 bladder cancer, which are specific biomarkers to be treated, or to a patient population diagnosed with stage III or IV ovarian cancer. In particular, the pharmaceutical composition may be administered to a patient population with chronic myelomonocytic leukemia (CML), a patient population with T-cell acute lymphoblastic leukemia (T-ALL), a patient population with chronic lymphocytic leukemia (CLL), a high-risk patient population with genomic abnormalities, a patient population with relapsed secondary AML (SAML), a patient population with treatment-related AML (t-AML) due to prior therapy, and drug-resistant/refractory patient population.

Hereinafter, the present invention is described.

As used herein, a drug is any substance (other than a food or device) used to diagnose, cure, mitigate, treat, or prevent disease, or to affect the structure or function of the body. For example, any chemical or biological substance that affects the body and its metabolism. The chemical name of a drug refers to the atomic or molecular structure of the drug.

In order for a drug to work effectively in the body, the concentration of the drug in the body must remain within the therapeutic range over a period of time. If there is too much of a drug in the body, it will be toxic, and if there is too little, it will have no therapeutic effect.

Drug efficacy is defined as the ability of a drug to remain in the body without being broken down for the expected amount of time to be effective for the target indication. A lower metabolism rate results in a longer duration of efficacy, as the drug remains in the blood for a longer period of time.

Cells, the basic building blocks of the body, regulate cell division and death to maintain tissue homeostasis, and active death is called apoptosis or programmed cell death. Apoptosis is a phenomenon in which the suicide mechanism inherent in the cell is activated by internal and external stimuli, and the cell dies as planned. Unlike necrosis, the contents of the dying cell do not escape into the extracellular space and cause damage to other cells. Morphologically, it refers to the process of phagocytosis with a decrease in the specific gravity of the cell, disruption of the cell membrane, and condensation of the chromosomes to form an apoptotic body, and biochemically, it refers to DNA fragmentation in which the chromosomal DNA is broken into smaller pieces from larger pieces.

In general, the mechanism of apoptosis is a series of signaling events that are triggered by the degradation of intracellular proteins by proteolytic enzymes called caspases, and several types of caspases are involved in apoptosis. Caspase-8 is activated by pro-apoptotic substances such as TNF-α or Fas ligand and triggers apoptosis by activating a series of other caspases. During apoptosis, cytochrome c is released through a channel in the mitochondrial membrane and is regulated by the BCL-2 family of proteins that comprise the channel. It has been reported that released cytochrome c binds to Apaf-1, caspase-9, and dATP to activate caspase-9, and caspase-9 activates caspase-3 to induce apoptosis (FIG. 9).

There are two factors that determine the growth of a tumor: cell proliferation and cell death. When the cell cycle of a tumor cell is arrested by a cytotoxic agent, the tumor cell dies due to apoptosis.

As shown in FIG. 9, B-cell lymphoma (BCL)-2 mediates apoptosis.

Although cancer therapies induce several types of cell death, activation of the apoptotic pathway regulated by BCL-2 is central to the therapeutic efficacy of oncogenic kinase inhibitors and cytotoxic agents. However, defects in the mitochondrial apoptotic pathway cause many cancers to develop resistance to cytotoxic drugs.

BCL-2 overexpression has been demonstrated in Chronic Lymphocytic leukemia (CLL) cells to mediate tumor cell survival and is associated with resistance to chemotherapeutic agents.

Venetoclax is a potent, selective, small molecule inhibitor of the anti-apoptotic protein BCL-2. In other words, venetoclax is an apoptosis-inducing anticancer drug. Venetoclax directly binds to the BH3-binding groove of BCL-2, displacing BH3-motif-containing pro-apoptotic proteins such as BIM, which, when unbound to BCL-2, initiates mitochondrial membrane permeabilization (MOMP), caspase activity, and apoptosis (FIG. 9). In nonclinical studies, the drug has shown cytotoxicity in tumor cells overexpressing BCL-2.

Since the standard regimen for AML treatment has recently changed from the monotherapy of decitabine/azacytidine to the combination of these drugs with the BCL-2 inhibitor venetoclax (trade name: Venclexta), the present inventors have evaluated the effectiveness of Aza-T-dCyd of the following formula 1 in place of Decitabine/Azacytidine when co-administered with the drug Venetoclax.

[Formula 1]

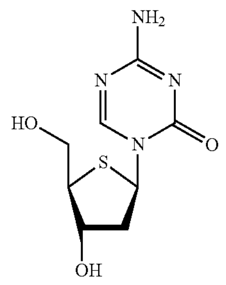

Surprisingly, in a xenograft model using the MV4-11 AML cell line subcutaneously implanted in mice, Aza-T-dCyd (NTX-301), even when treated alone at clinically relevant concentrations, exhibited anti-cancer efficacy equivalent to or superior to that of Azacytidine/Venetoclax combination by reducing the expression of anti-apoptotic proteins such as Survivin and Mcl-1 through potent p53 activation, while the combination of Aza-T-dCyd and Venetoclax showed strong cancer growth inhibition compared to Azacytidine/Venetoclax, even at very low drug doses (Aza-T-dCyd 0.5 mpk induced complete tumor regression) and very strong anti-cancer efficacy (FIG. 28 to FIG. 33). It can be inferred that both Aza-T-dCyd and Venetoclax inhibit the action of anti-apoptotic proteins when administered in combination. The present invention is based on this.

In the present invention, the drug co-administered with the Aza-T-dCyd drug is not limited to the compound of formula 2 below (venetoclax) as long as it is a BCL-2 inhibitor, and falls within the scope of the present invention.

[Formula 2]

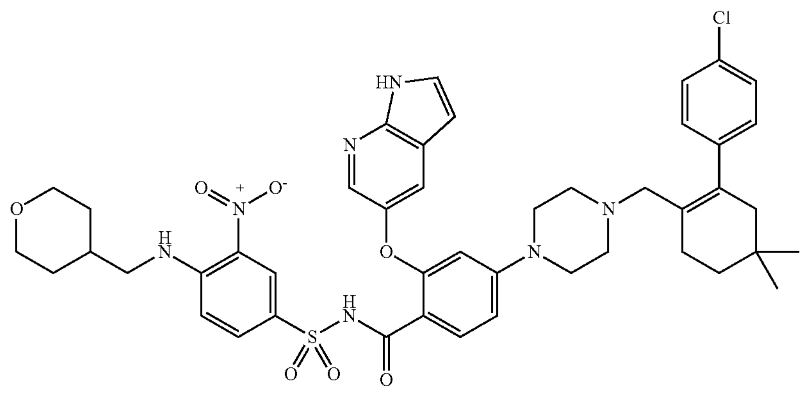

The present invention is characterized by the selection of Aza-T-dCyd of formula 1 as a DNMT1 inhibitor for combination treatment with the drug venetoclax, based on the analysis of the mechanism of action of existing nucleoside-based anticancer drugs and the activation of DNA damage repair, which is the mechanism of resistance.

DNMT1 inhibitors, which inhibit the action of anti-apoptotic proteins, may be a very promising approach to overcome existing Decitabine/Azacytidine resistance. Therefore, the present invention is to select Aza-T-dCyd of formula 1 as a DNMT1 inhibitor in the process of molecularly designing a well-designed multi-target inhibitor that exhibits potent anticancer efficacy by potent inhibition of the main drug target DNMT1 and simultaneous blocking of its hydrolysis by endonuclease, an existing mechanism of resistance development, through a multi-pharmacological approach, and to use it in combination therapy with the drug venetoclax.

Aza-T-dCyd, formula 1, is a DNMT1 inhibitor based on the 4-Thio-2-deoxyribose backbone, which has a sugar structure change (4'-thiodeoxyribose structure) and an Aza-cytosine group. Molecular modeling has shown that thio-deoxyribose-based nucleoside compounds do not significantly affect other DNA components after insertion into DNA.

Aza-T-dCyd is a nucleoside anticancer drug that is activated in the triphosphate form in cells to replace some of the deoxycytidine (dC) in DNA synthesis and traps DNMT1 after DNA synthesis to induce cancer cell death by activating various epigenetic mechanisms of action. In particular, Aza-T-dCyd is rapidly activated in cancer cells, incorporates into DNA, and can trap and inhibit the DNMT1 enzyme even at low concentrations.

As shown in FIG. 5, nucleoside-based anticancer drugs exert their anticancer efficacy through various mechanisms of action after DNA incorporation (inhibition of DNA synthesis/transcription, induction of DNA damage, or expression of pharmacological effects through inhibition of DNA processing-related enzymes such as DNMT1).

As shown in FIG. 6, nucleoside-based anticancer drugs form base pairs that do not match normal DNA components during DNA incorporation, causing abnormal structures in DNA, which are recognized by BER (Base Excision Repair), a DNA damage repair method, and DNA damage repair is performed.

At the beginning of the administration of nucleoside-based anticancer drugs, cancer cells are efficiently killed by exerting sufficient pharmacological effects after incorporation of anticancer drugs into DNA, but as the administration of anticancer drugs continues, BER is overactivated and these anticancer drugs are removed before they have sufficient effect, resulting in resistance to anticancer drugs.

Therefore, the present invention, which has selected Aza-T-dCyd of formula 1 as a DNMT1 inhibitor that can be used in combination therapy with the drug venetoclax, is based on the idea that a new nucleoside-based compound that can be incorporated into DNA with an efficiency equal to or greater than that of existing nucleoside-based anticancer drugs, and that is resistant to BER while expressing the desired pharmacological effects, is expected to show stronger efficacy than existing anticancer drugs.

The first step in BER is to break the glycosidic bonds in the nucleoside/nucleotide to create a base-free site, which is then used by endonuclease to create a site where DNA damage is repaired, and then various enzymes fill in other complementary bases with opposite base information to repair the DNA damage (FIG. 6).

Since the speed and efficiency of the BER repair process is determined by the recognition of the abnormal base pair, the breaking of the C—N bond, and the creation of a vacant nucleotide site by the AP-endonuclease, impairing one or more of these steps can reduce the efficiency of BER and thus inhibit the development of resistance due to overactivation of BER.

Since nucleoside compounds with a 4-Thio-2-deoxyribose backbone are resistant to DNA strand cleavage by endonucleases, and this mechanism is the first step in the DNA-damage repair pathway, DNMT1 inhibitors with a 4-Thio-2-deoxyribose backbone can overcome drug resistance caused by anti-apoptotic proteins and the DNA-damage repair pathway. Therefore, Aza-T-dCyd (NTX-301) has strong anti-cancer efficacy/resistance overcoming potential compared to existing DNMT1 inhibitors due to its 4-Thio-2-deoxyribose backbone (Example 1 and Example 2).

On the one hand, the BER mechanism of action acts as a mechanism for the development of resistance in cancer cells, but on the other hand, in normal tissues (especially hematopoietic tissues such as bone marrow), it acts as a safety mechanism to prevent toxicity caused by anticancer drugs, so there is a high need for anticancer drugs that inhibit BER to be delivered selectively to cancer cells.

After entering the cell, nucleoside-based anticancer drugs are activated by various nucleoside kinases to accumulate in the cell, and nucleoside compounds that are not activated within a reasonable time are quickly eliminated. Maximizing the difference between the activation rate in normal cells and cancer cells can ensure excellent safety by accumulating the active form of the drug only in cancer cells.

Existing literature reports that nucleosides substituted with various heteroatoms can be activated or eliminated through metabolism at different rates, and among them, thio-deoxyribose can be activated at a relatively slow rate in normal cells, while cancer cells can be activated at a rate equivalent to or higher than normal deoxyribose-based nucleosides and used for DNA synthesis. This may lead to a selective drug delivery effect as it accumulates relatively more in cancer cells than in normal cells.

Aza-T-dCyd utilizes a thio-deoxyribose backbone, which is an improvement on the existing deoxyribose backbone, and compared to deoxyribose-based nucleosides such as Decitabine, it is rapidly activated and efficiently incorporated into DNA in cancer cells, but slowly activated in normal organs including normal bone marrow cells, enabling selective drug delivery to cancer cells; By being affected relatively slowly by the main metabolic enzyme of nucleoside anticancer drugs called Cytidine Deaminase, it not only secures the possibility of overcoming metabolism-related resistance, but also forms a longer-lasting DNA-DNMT adduct after incorporation and DNMT1 trapping through an azacytosine functional group that can well trap the DNMT1 enzyme, securing stronger and differentiated effects.

Unlike Decitabine/Azacytidine with the chemical structure as shown in FIG. 4, Aza-T-dCyd with the formula 1, due to its thio-nucleoside structure, exhibits strong anticancer efficacy by simultaneously blocking the strong inhibition of DNMT1, the main drug target, and hydrolysis by endonuclease, the existing mechanism of resistance development, It was confirmed that it has an excellent PK profile in oral administration as well as metabolic resistance by cytidine deaminase, and is applicable to hematologic and solid cancers (ovarian/bladder cancer) (Example 1 to Example 4).

In addition, deoxycytidine-based compounds used in the chemotherapy of cancer or viral infections require phosphorylation by cellular enzymes to be activated. Phosphorylation of deoxycytidine compounds by deoxycytidine kinase (dCK) is considered to be the rate-limiting step in the activation of the compound, followed by further phosphorylation to diphosphate or triphosphate. Due to its thio-nucleoside structure, Aza-T-dCyd has a significantly lower rate of activation by deoxycytidine kinase (dCK) in normal cells, thereby selectively delivering the active ingredient of the drug to cancer cells and securing an excellent safety profile, thus securing a wide therapeutic window, and can be administered at high doses to prevent the development of resistance mechanisms.

Aza-T-dCyd compounds can be rapidly triphosphorylated in cancer cells compared to normal cells. Aza-T-dCyd compounds can delay DNA replication by causing base excision repair and/or mismatch repair through DNA insertion of aza-T-dCTP, the triphosphate of aza-T-dCyd compounds, thereby causing replication stress and exacerbating the DNA damage response.

Aza-T-dCyd compounds can inhibit RRM1 protein expression, a ribonucleotide reductase important for dNTP de novo synthesis, and reduce intracellular dCTP and dTTP amounts, leading to DNA replication stress and a strong DNA damage response.

Unlike Decitabine/Azacytidine, aza-T-dCyd, due to its thio-nucleoside structure, can exhibit potent anticancer efficacy by simultaneously blocking nucleic acid endonucleases that participate in DNA damage repair, an existing mechanism of resistance development, along with strong inhibition of DNMT1, the main drug target (FIG. 6).

Decitabine/Azacytidine is susceptible to metabolism by cytidine deaminases in the body, resulting in an unstable PK profile that limits its efficacy. Surprisingly, we found that compared to Decitabine/Azacytidine, aza-T-dCyd and aza-T-dCTP have a slower rate of degradation by cytidine deaminase when administered orally, and thus have a superior PK profile when administered orally as well as overcoming metabolic resistance by cytidine deaminase in cancer cells (Example 3).

In addition, due to its thio-nucleoside structure, aza-T-dCyd has a significantly lower rate of activation by deoxycytidine kinase (dCK) in normal cells, resulting in selective delivery of the drug's active ingredient to cancer cells, thereby securing an excellent safety profile and securing a wide therapeutic window, so it can be administered at a high dose that prevents the mechanism of resistance development from operating.

Furthermore, through pharmacokinetic characterization, we found that (1) the anticancer effect of aza-T-dCyd is Cmax-dependent rather than AUC-dependent; and (2) exposure to a higher dose of aza-T-dCyd drug for a shorter period of time is an efficient anticancer treatment.

At the cellular level, Aza-T-dCyd induces significantly improved changes in drug efficacy markers (PD markers) compared to Decitabine/Azacytidine, resulting in more potent cancer cell death induction than Decitabine/Azacytidine (Example 1).

Furthermore, these enhanced PD marker changes allow it to maintain its superior cancer cell death inducing activity even in cell lines resistant to decitabine. These effects at the cellular level translate into superior efficacy in animal models, where Aza-T-dCyd has shown excellent anti-cancer activity in a variety of animal models where Decitabine/Azacytidine has shown no therapeutic benefit.

Aza-T-dCyd has an orally bioavailable PK profile and a superior safety profile to conventional decitabine/azacytidine in GLP preclinical toxicity studies.

In particular, a high disease control rate at the 32 mg/day dose was confirmed in clinical trials, and animal models of the disease group (AML, T-ALL, various solid cancers) were tested at doses with similar drug exposure in animal trials, and all showed excellent efficacy compared to existing competing drugs.

In particular, in a Phase 1a clinical trial of Aza-T-dCyd in solid tumors conducted by the National Cancer Institute, no significant side effects were observed when Aza-T-dCyd was administered at a dose approximately twice that of conventional decitabine, and the efficacy and safety of Aza-T-dCyd in humans were also secured, including an excellent PK profile when administered orally and the identification of robust PD markers in circulating tumor cells. Even at very low doses, it was observed to slow down disease progression in cancer patients, showing superior efficacy compared to existing drugs.

Thus, Aza-T-dCyd could be a DNMT1 inhibitor with stronger efficacy, improved safety profile, ease of use, and potential to overcome drug resistance compared to existing DNMT1 inhibitors that are the standard of care.

On the other hand, venetoclax can be administered up to 250 mg/day, and the dose of Aza-T-dCyd in combination with venetoclax can be less than 32 mg/day, e.g., 8 mg/day or more but less than 32 mg/day, preferably 8 to 24 mg/day. 24 mg corresponds to 1.5 mpk.

In combination with a venetoclax drug, the Aza-T-dCyd drug may be administered at a dose of 25% to 75% of the maximum tolerated dose (MTD).

In Phase 1 clinical trials, which are first conducted in humans after preclinical studies to monitor the response for toxicity and adverse events, the primary objective is to determine the MTD, which is the maximum dose that can be tolerated by subjects without causing adverse events.

Aza-T-dCyd shows potent anti-cancer activity in animal models at doses as low as 0.5 mg/kg (mpk), and drug exposure at these doses can be as low as 8 mg/day in humans (25% of the MTD in Phase 1), providing a wide therapeutic window.

When comparing the efficacy of Aza-T-dCyd to the current standard of care for AML, Azacytidine in combination with the BCL-2 inhibitor Venetoclax (trade name: Venclexta), the Aza-T-dCyd 2.0 mpk monotherapy group (equivalent to the MTD dose of 32 mg of Aza-T-dCyd in Phase 1) was found to be as effective as the Azacytidine/Venetoclax group, while the Aza-T-dCyd 0.5 or 1.0 m.p.k. (25-50% of the MTD dose of 32 mg in Phase 1) in combination with Venetoclax showed significantly stronger activity compared to the standard of care (Azacytidine/Venetoclax combination) (FIGS. 28 to 33).

For the existing same mechanism drug Decitabine/Azacytidine, a 50% dose reduction from the MTD was required for coadministration with Venetoclax, and a dose reduction to 25% of the MTD showed good safety but weak efficacy. In the case of Aza-T-dCyd, dose reduction to 25% of the MTD and co-administration with Venetoclax resulted in significantly better efficacy than the Azacytidine/Venetoclax group, suggesting that Aza-T-dCyd is likely to have superior safety/efficacy in humans compared to the existing standard of care (Example 5).

In the present invention, the compound of formula 1 and the compound of formula 2 may each independently exist in solid or liquid form. In the solid state, they may exist in crystalline or amorphous form, or as mixtures thereof. In the case of crystalline or non-crystalline compounds, pharmaceutically acceptable solvates may be formed. In crystalline solvates, the solvent molecules are incorporated into the crystalline lattice during crystallization. The solvate may comprise a non-aqueous solvent such as, but not limited to, ethanol, isopropanol, DMSO, acetic acid, ethanolamine, or ethyl acetate, or they may comprise water as the solvent incorporated into the crystalline lattice. Solvates in which water is the solvent incorporated into the crystalline lattice are typically referred to as "hydrates". Hydrates include stoichiometric hydrates as well as compositions containing variable amounts of water. The present invention encompasses all solvates, including such hydrates.

Certain compounds of the present invention, including their various solvates, which exist in crystalline form, may exhibit polymorphism (i.e., the ability to occur in different crystalline structures). These different crystalline forms are typically known in the "polymorphs". The present invention encompasses all such polymorphs. Polymorphs have the same chemical composition, but differ in packing, geometric arrangement, and other descriptive characteristics of the crystalline solid state. Thus, polymorphs can have different physical properties, such as shape, density, hardness, deformability, stability, and dissolution properties. Polymorphs typically exhibit different melting points, IR spectra, and X-ray powder diffraction patterns, which can be used for identification. Different polymorphs can be prepared, for example, by changing or adjusting the reaction conditions or reagents used in the preparation of the compound. For example, changes in temperature, pressure, or solvent can produce polymorphs. Additionally, one polymorph can spontaneously convert to another polymorph under certain conditions.

As used herein, the drug 4'-thio-5-aza-2'-deoxycytidine (aza-T-dCyd) includes the compound of Formula 1, as well as pharmaceutically acceptable salts thereof, solvates thereof, and prodrugs thereof.

The term "pharmaceutically acceptable salt" refers to a pharmaceutically acceptable organic or inorganic salt. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate) salt). A pharmaceutically acceptable salt may further comprise the inclusion of another molecule, such as an acetate ion, a succinate ion, or another counterion. The counterion can be any organic or inorganic moiety that stabilizes the charge on the parent compound. Furthermore, a pharmaceutically acceptable salt may have more than one charged atom in its structure. If multiple charged atoms are part of a pharmaceutically acceptable salt, it may have multiple counter ions. Thus, a pharmaceutically acceptable salt may have one or more charged atom and/or one or more counter ion.

"Prodrug" has the meaning as it is used in the art. For example, a compound chemically modified from a physiologically active substance or therapeutically active organic compound and designed to free or release the parent compound under enzymatic or other conditions in vivo. After administration, prodrugs are transformed in vivo into the target compound. A prodrug is a drug that is useful but has unsuitable properties in terms of side effects, stability, solubility, absorption, or duration of action, and is made clinically available by chemical modification.

"Solvate" means a compound of formula 1 or a salt thereof that additionally contains a stoichiometric or non-stoichiometric amount of solvent bound by non-covalent intermolecular forces. If the solvent is water, the solvate is a hydrate.

As used herein, "cancer" refers to a mammalian physiological condition typically characterized by uncontrolled cell growth. Examples of cancer include, but are not limited to, blood-borne tumors (e.g., multiple myeloma, lymphoma, and leukemia) and solid tumors. Non-limiting examples of blood cancers include non-Hodgkin's lymphoma, Hodgkin's lymphoma, multiple myeloma, leukemia, lymphoma, myelodysplastic syndrome, acute lymphocytic leukemia, acute myeloid leukemia, and chronic myeloid leukemia, and non-limiting examples of solid tumors include stomach cancer, kidney cancer, ovarian cancer, cervical cancer, uterine cancer, prostate cancer, lung cancer, colon cancer, breast cancer, melanoma, and pancreatic cancer.

As used herein, "patient," "subject," and "subject matter" refer to an animal, such as a mammal. In certain embodiments, a patient is a human. In other embodiments, the patient is a non-human animal, such as a dog, cat, livestock (e.g., horse, pig, or donkey), chimpanzee, or monkey.

As used herein, an anticancer effect or therapeutic effect of an anticancer agent may refer to an action that reduces the severity of a cancer, reduces the size of a tumor, or delays or slows the progression of a cancer, that occurs while a patient is suffering from a particular cancer.

For example, an anticancer effect caused by an anticancer agent may be a change in cell viability (degree of cytotoxicity or change in cell number) of a cancer cell after the cancer cell is treated with the anticancer agent in-vitro and/or in-vivo. It can be determined indirectly, for example, by testing drug response in cell lines or non-clinical animal models (xenografts). In addition, the anti-cancer effect of anticancer drugs can be directly confirmed in cancer patients, and related data can be derived and used as a database. In addition, animal model PK parameters and/or toxicity profiles can be considered in parallel when designing dosing guidelines for anticancer drugs.

The anticancer effect of an anticancer drug can be inferred from in vitro data such as the % Maximum effect of the drug, e.g., $IC_{50}$, $IC_{60}$, $IC_{70}$, $IC_{80}$ and $IC_{90}$, or from in vivo data such as the peak blood concentration of the drug (Cmax) and/or the area under the blood drug concentration-time curve (AUC) in non-clinical animal models and clinical cancer patients.

The reactivity of an anticancer drug refers to its clinical sensitivity in terms of anticancer effect.

When referring to treatment with an anticancer drug, "sensitivity" and "sensitive" are relative terms that refer to the degree of effectiveness of a compound in alleviating or reducing the progression of the tumor or disease being treated.

"Effective patient anti-cancer effect/response" may be, for example, a 5%, 10%, 15%, 20%, 25%, 30%, 40%, 50%, 60%, 70%, 80%, 90%, 100%, 200%, or greater inhibition in patient response, as measured by any suitable means, e.g., gene expression, cell counting, assay results, etc.

As used herein, a dosage is a dose at which a pharmaceutical effect is expected. In the present invention, the pharmaceutical effect may be an anti-cancer effect. The reactivity (anticancer effect) of an anticancer agent may be a degree of reactivity, such as the % Maximum effect of that anticancer agent, e.g., $IC_{50}$, $IC_{60}$, $IC_{70}$, $IC_{80}$ and $IC_{90}$, or the value at which it exerts toxicity against normal cells ($LC_{50}$).

For example, the oral formulation may be formulated using various formulation techniques known in the art. For example, it may include a biodegradable (hydrolyzable) polymeric carrier used to adhere to the oral mucosa. They are formulated to erode gradually over a scheduled period of time, where drug delivery is essentially provided in its entirety.

In oral formulations, drug delivery avoids the weaknesses encountered with oral drug administration, such as slow absorption, degradation of the active agent by fluids present in the gastrointestinal tract, and/or first-pass inactivation in the liver. For biodegradable (hydrolyzable) polymeric carriers, virtually any such carrier may be used as long as the desired drug release profile is not compromised, and the carrier is compatible with any other ingredients present in the oral dosage unit. In general, polymeric carriers include hydrophilic (water-soluble and water-swellable) polymers that adhere to the wetted surface of the oral mucosa. Examples of polymeric carriers useful herein include acrylic acid polymers (e.g., carbomers). In some embodiments, non-limiting examples of other ingredients that may be incorporated into an oral formulation include disintegrants, diluents, binders, lubricants, flavoring agents, coloring agents, preservatives, and the like. In some embodiments, the formulation may be in the form of conventionally formulated tablet, lozenge, or gel for oral or sublingual administration.

In some embodiments, administration of the compound may be continued at the discretion of the physician if the patient's condition improves; alternatively, the dose of the drug to be administered may be temporarily reduced or temporarily discontinued for some length of time (i.e., a "washout"). The length of the washout period can vary from 2 days to 1 year and includes, by way of example, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. In some implementations, the dose reduction during the washout period is 10%-100%, and includes, by way of example only, 10%, 15%, 20%, 25%, 30%, 35%, 40%, 45%, 50%, 55%, 60%, 65%, 70%, 75%, 80%, 85%, 90%, 95%, or 100%.

If improvement in the patient's condition occurs, maintenance dose is administered, if necessary. Thereafter, the dose or frequency of administration, or both, may be reduced as a function of symptoms, to a level at which the improved disease, disorder, or condition is maintained. However, the patient may require intermittent treatment over an extended period of time at any recurrence of symptoms.

The amount of a given formulation that will correspond to such an amount will vary depending on factors such as the particular compound, the severity of the disease, and the identity (e.g., weight) of the subject in need of treatment, but may nevertheless be routinely determined in a manner known in the art, for example, based on the formulation to be administered, the route of administration, and the particular circumstances surrounding the subject to be treated. In general, however, doses utilized in the treatment of adult humans will typically be in the range of 0.02-5000 mg/day, or about 1-1500 mg/day.

As used herein, a single dose may be provided as a single dose or as a divided dose administered simultaneously, for example in two, three, four or more sub-doses.

In some embodiments, the oral formulation is a unit dosage form suitable for single administration of a precise dose. In a unit dosage form, the formulation is divided into unit doses containing appropriate amounts of one or more compounds. In some embodiments, the unit dose is in the form of a sachet containing a distinct amount of the formulation. Non-limiting examples are packaged tablets or capsules, and powder in vials or ampoules. The aqueous suspension composition may be packaged within a single-dose non-reclosable container. Alternatively, multi-dose reclosable containers may be used, in which case the composition typically includes a preservative.

In some embodiments, parenteral injectable formulations are provided in unit dose forms, including, without limitation, ampoules, or multi-dose containers with an added preservative.

Unit-dose injectable forms are typically formulated for parenteral administration, i.e., bolus, intravenous, and intratumoral injections, with a pharmaceutically acceptable parenteral vehicle. It is freely admixed with pharmaceutically acceptable diluents, carriers, excipients, or stabilizers (Remington's Pharmaceutical Sciences (1980) 16th edition, Osol, A. Ed.) to form lyophilized preparations or aqueous solutions.

Advantageous Effects

Aza-T-dCyd is a thio-nucleoside compound that changes the deoxyribose structure of nucleoside anticancer drugs to a thio-deoxyribose structure, and through this change, it can overcome the limitations of existing nucleoside-based anticancer drugs and meet unmet needs by having the following features.

(1) By forming a longer-lasting DNMT1 trapping complex due to the thio-nucleoside structure, it has differentiated strong anti-cancer efficacy compared to Decitabine (trade name: Dacogen) and Azacytidine (trade name: Vidaza) and it has secured the possibility of overcoming resistance in resistant AML patients;

(2) Securing an excellent safety profile by selectively delivering the active ingredient of the drug to cancer cells by significantly lowering the activation rate by dCK (deoxycytidine kinase) in normal cells due to its thio-nucleoside structure;

(3) slower rate of degradation by cytidine deaminase when administered orally compared to conventional decitabine/azacytidine, thus securing the possibility of overcoming resistance due to metabolism in cancer cells and the possibility of oral administration; and (4) safety and oral PK profile through administration in humans.

In addition, Aza-T-dCyd's potent efficacy and differentiated safety profile, attributable to its thio-nucleoside backbone, may lead to expanded indications compared to traditional DNMT1 inhibitors (traditional DNMT1 inhibitors (MDS/AML-focused) VS. Aza-T-dCyd (expanded to various hematologic and solid tumors)), superior efficacy in various situations where conventional DNMT1 inhibitors do not show drug efficacy (such as strong efficacy in solid tumor patients in Phase I), and superior safety (nonclinical and Phase I results), showing clear competitive advantages in terms of efficacy and safety.

Thus, the combination therapy of 4'-thio-5-aza-2'-deoxycytidine (Aza-T-dCyd), a multi-target inhibitor including DNMT1 inhibitor, and Venetoclax, an inhibitor of BCL-2 that mediates apoptosis, according to the present invention, is versatile in terms of administration, dose, or target patient population.

BEST MODE FOR CARRYING OUT THE INVENTION

Hereinafter, the present invention will be described in more detail through examples. However, the following examples are intended to clearly illustrate the technical features of the present invention and do not limit the scope of protection of the present invention.

Example 1: In Vitro Pharmacology 1-1. DNMT1 Inhibition

An important drug efficacy marker (PD marker) for Aza-T-dCyd is the inhibition of the drug target DNMT1 and a decrease in the intracellular amount of DNMT1 protein.

Cytidine-like structural nucleoside DNMT1 inhibitors such as decitabine are known to incorporate into DNA, irreversibly trap DNMT1 and induce its degradation through protease complexes, and it has been established through various basic and clinical studies and the utilization of DNMT1 inhibitors in patients that loss of DNMT1 protein promotes the expression of pro-differentiation/anti-cancer genes.

1-1-1. Confirmation of Decreased Intracellular DNMT1 Protein in AML Cell Lines

Figure 10:
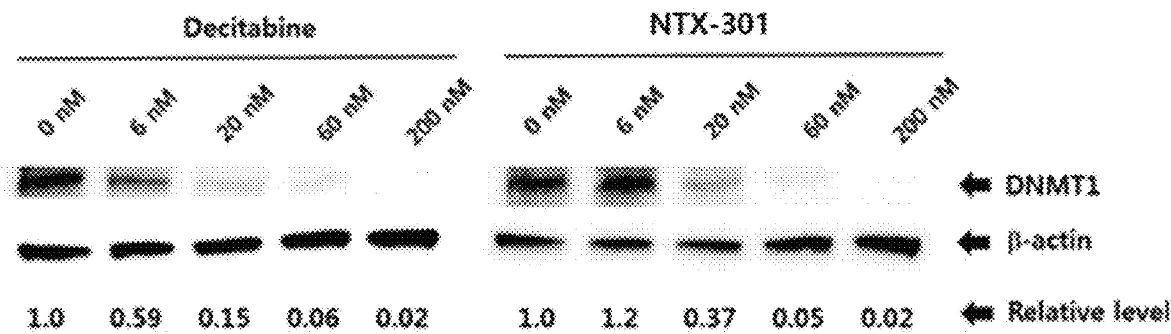
FIG. 10 shows that treatment of MV4-11 (AML cell line) cells with NTX-301 (SRI-9639) and Decitabine at different concentrations inhibits DNMT1.
Figure 11:
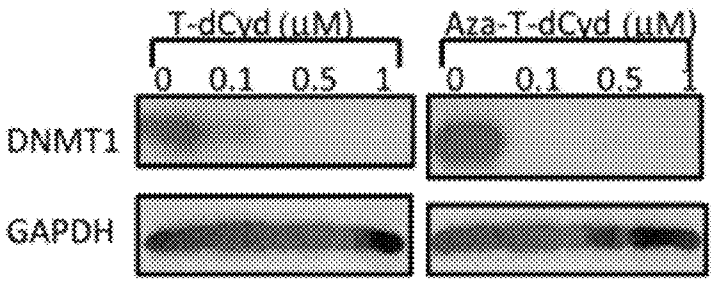
FIG. 11 shows that treatment of KG-1a (AML cell line) cells with NTX-301 (Aza-T-dCyd) and T-dCyd inhibits DNMT1.

To evaluate the DNMT1 inhibition efficacy of Aza-T-dCyd in AML cell lines, standard AML cell lines MV4-11 (FIG. 10) and KG-1a (FIG. 11) were treated with Aza-T-dCyd and a positive control, Decitabine, and Western blotting for DNMT1 protein was performed. As shown in FIGS. 10 and 11, we found that Aza-T-dCyd reduced DNMT1 protein in a concentration-dependent manner in both cell lines. Notably, even at a very low concentration of 20 nM, it completely reduced DNMT1.

1-1-2. ALL Cell Line/Solid Cancer Cell Line

Figure 12:
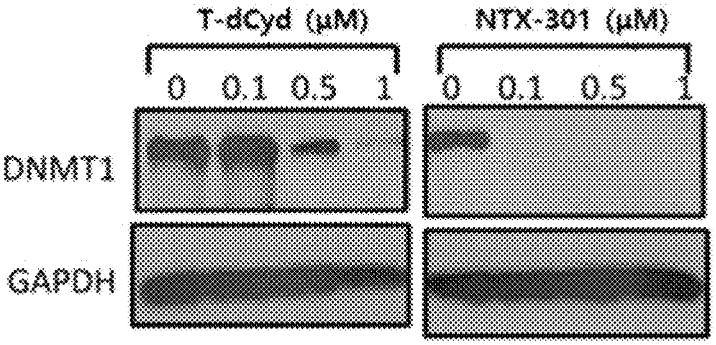
FIG. 12 shows that treatment of CCRF-CEM (ALL cell line) cells with NTX-301 and T-dCyd inhibits DNMT1.
Figure 13:
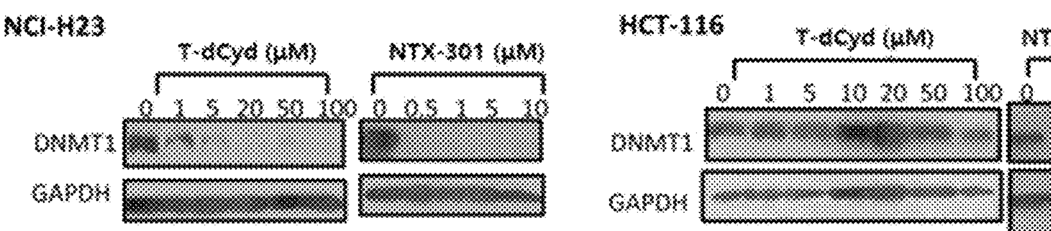
FIG. 13 shows that treatment of NCI-H23 (Lung carcinoma cells), HCT-116 (Colon carcinoma cells), and IGROV-1 (Ovarian carcinoma cells) cell lines with NTX-301 and T-dCyd inhibits DNMT1.
Figure 13:
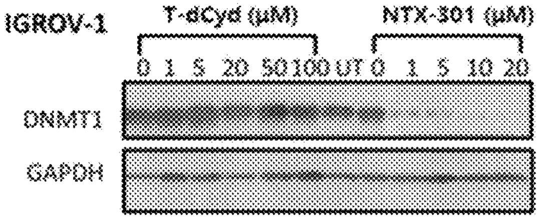

The same DNMT1 inhibitory efficacy evaluation was performed in other blood cancer cell lines, ALL cell line and solid cancer cell line, and confirmed that Aza-T-dCyd (NTX-301) can inhibit DNMT1 in a concentration-dependent manner in CCRF-CEM (ALL) (FIG. 12) and solid cancer cell line (FIG. 13).

1-2. Cellular Pharmacodynamics 1-2-1. Identification of Re-expression of the p15 Tumor Suppressor Gene.

In the DNA of hematopoietic stem cells of MDS and AML patients, many cytosines in the promoter region of many tumor suppressor genes are methylated and their expression is suppressed, resulting in inhibition of important functions such as DNA damage repair and cell cycle checkpoints compared to normal.

Abnormal DNA methylation of many tumor suppressor genes has been reported in many types of leukemia, including AML, and in particular, inactivation of p15 tumor suppressor genes due to CpG island hypermethylation induces abnormal cell proliferation.

Treatment with epigenetic modifying drugs that can normalize the methylation of DNA, such as Decitabine, which normalizes the methylation pattern, causes these hematopoietic stem cells to differentiate or die, which can be useful in the treatment of MDS/AML patients, and induces the re-expression of the intracellular PD marker p15. Through existing decitabine/azacytidine clinical trials and patient treatment, p15 re-expression in cancer cells and cancer patients with p15 silencing has been established as a PD marker to monitor the pharmacodynamic response of DNMT1 inhibitors.

Figure 14:
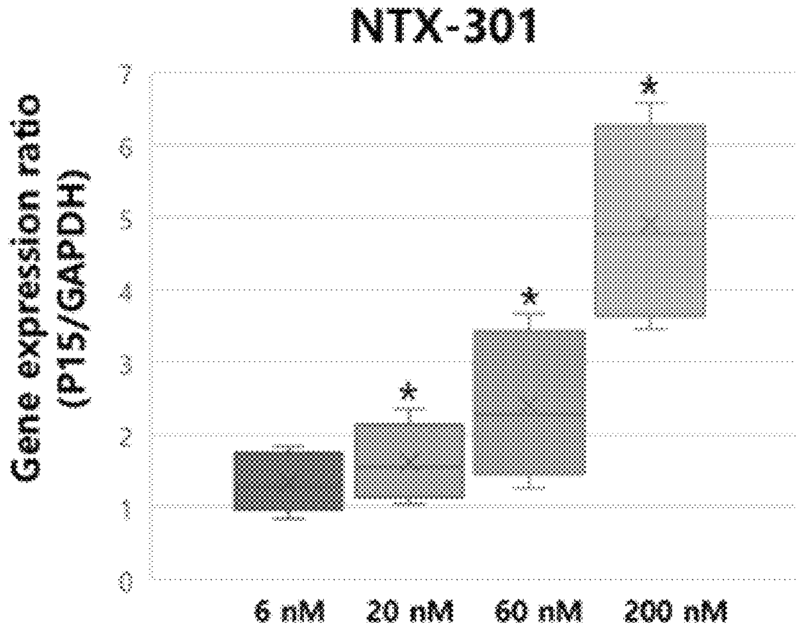
FIG. 14 shows the re-expression of the p15 tumor suppressor gene due to DNMT1 inhibition upon treatment of MV4-11 cells with Aza-T-dCyd.

Therefore, to determine the re-expression of tumor suppressor genes through epigenetic regulation mechanisms induced by DNMT1 inhibition upon Aza-T-dCyd (NTX-301) treatment, MV4-11 cells, an AML cell line, were treated with Aza-T-dCyd at different concentrations. The re-expression of the p15 tumor suppressor gene, a PD marker induced by DNMT1 inhibition, was confirmed, and RT-PCR confirmed the strong re-expression of p15 mRNA (FIG. 14).

Figure 15:
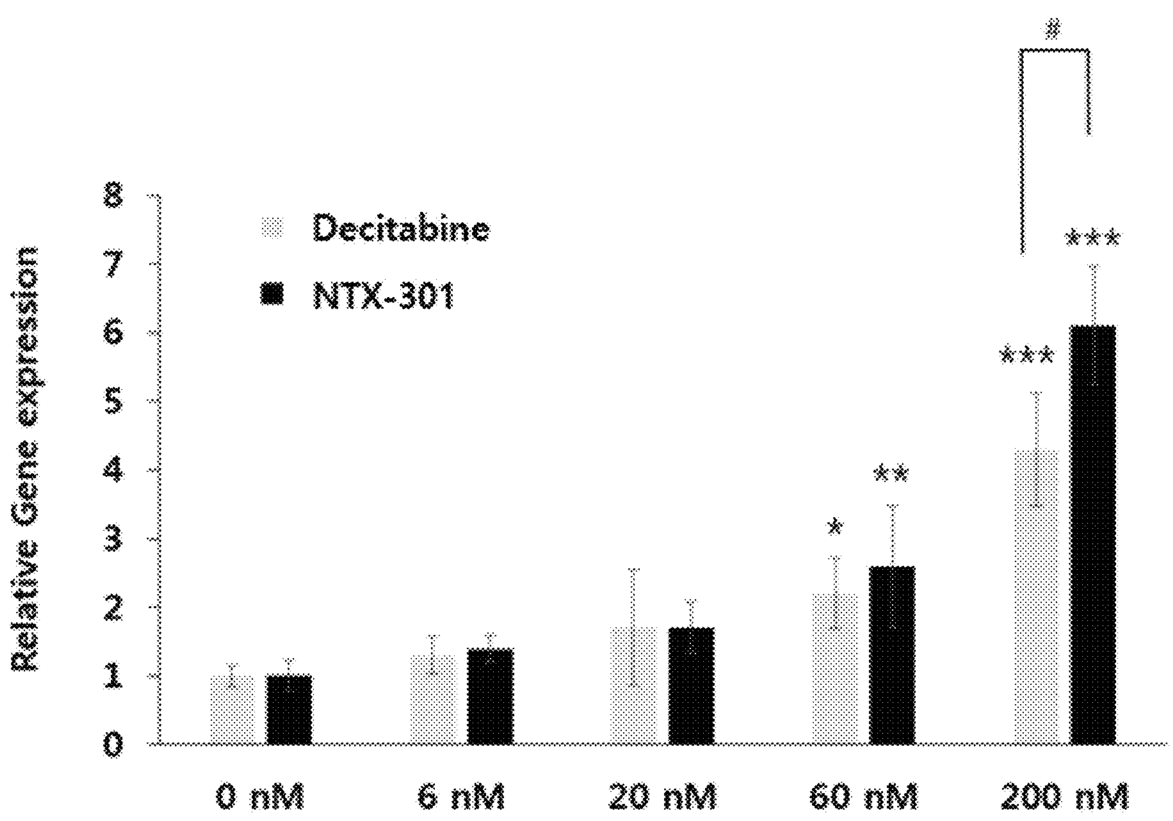
FIG. 15 is a comparative analysis of the re-expression of the p15 tumor suppressor gene due to DNMT1 inhibition upon treatment of MV4-11 cells with Aza-T-dCyd and Decitabine.

To compare the efficacy of DNMT1 inhibitors in MV4-11 cells, we performed quantitative RT-PCR to check the expression of p15 tumor suppressor gene upon treatment with Aza-T-dCyd (NTX-301) and Decitabine, and found that the expression of p15 tumor suppressor gene was significantly increased upon treatment with Aza-T-dCyd at concentrations of 60 nM and 200 nM (FIG. 15 and Table 1).

Table 1 below compares the degree of p15 mRNA re-expression after DNMT1 inhibitor (Aza-T-dCyd/Decitabine) treatment in the MV4-11 cell line, an AML cell (fold increase from 0 nM is shown).

TABLE 1

| | 0 nM | 6 nM | 20 nM | 60 nM | 200 nM |
|---|---|---|---|---|---|
| NTX-301 | 1.0 ± 0.23 | 1.4 ± 0.19 | 1.7 ± 0.38 | 2.6 ± 0.89 | 6.1 ± 0.86 |
| Decitabine | 1.0 ± 0.15 | 1.3 ± 0.27 | 1.7 ± 0.85 | 2.2 ± 0.52 | 4.3 ± 0.83 |

Furthermore, we found that Aza-T-dCyd induced p15 upregulation better than decitabine.

Therefore, the reduction of DNMT1 and re-expression of the p15 tumor suppressor gene upon treatment with Aza-T-dCyd suggest that Aza-T-dCyd may be a novel targeted anti-cancer agent.

1-2-2. Identify Changes in Additional PD Markers (CEBP/Epsilon, CDKN1B)

The problem with malignant cells from MDS/CMML/AML patients is that they express the lineage commitment Master TEs CEBP/alpha, Pu.1, and GATA factors at high levels, while the expression of late developmental transcription factors, including CEBP/epsilon, remains low due to hypermethylation of each gene.

CEBP/epsilon is a protein that induces maturation of immature hematopoietic cells and inhibits abnormal proliferation, and its induction leads to increased expression of CDKN1B and Myc antagonists (MADs). CDKN1B is a CDK inhibitor protein whose function is to arrest cell cycle proliferation or induce differentiation. This expression of CEB/epsilon and CDKN1B induces the differentiation of AML malignant cells and exhibits potent anti-cancer activity.

It has been reported that decitabine treatment inhibits DNMT1 to induce DNA demethylation and re-expression of CEBP/epsilon to cause apoptosis and cell differentiation, thereby showing excellent anticancer efficacy.

Figure 16:
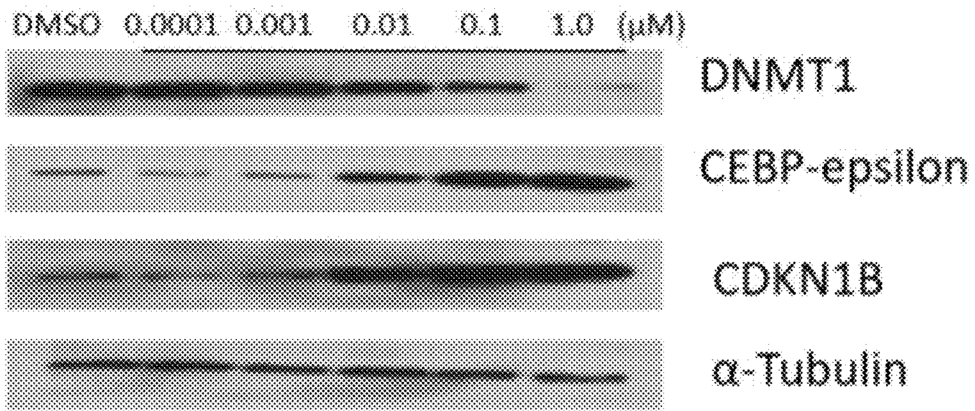
FIG. 16 shows the induced CEBP/epsilon expression upon concentration-dependent treatment of THP-1 cells with NTX-301 (Aza-T-dCyd).

CEBP/epsilon and CDKNIB expression was identified and comparatively analyzed in various AML cell lines to determine the mode of target engagement induced by DNMT1 inhibition upon treatment with Aza-T-dCyd (NTX-301) (FIG. 16).

Treatment of THP-1 cells, an AML cell line, with Aza-T-dCyd at different concentrations induced DNMT1 inhibition in a dose-dependent manner and correlated with increased CEBP/epsilon expression and CDKN1B expression, confirming the maturation-inducing and differentiation-inducing functions of Aza-T-dCyd in immature hematopoietic cells.

Figure 17:
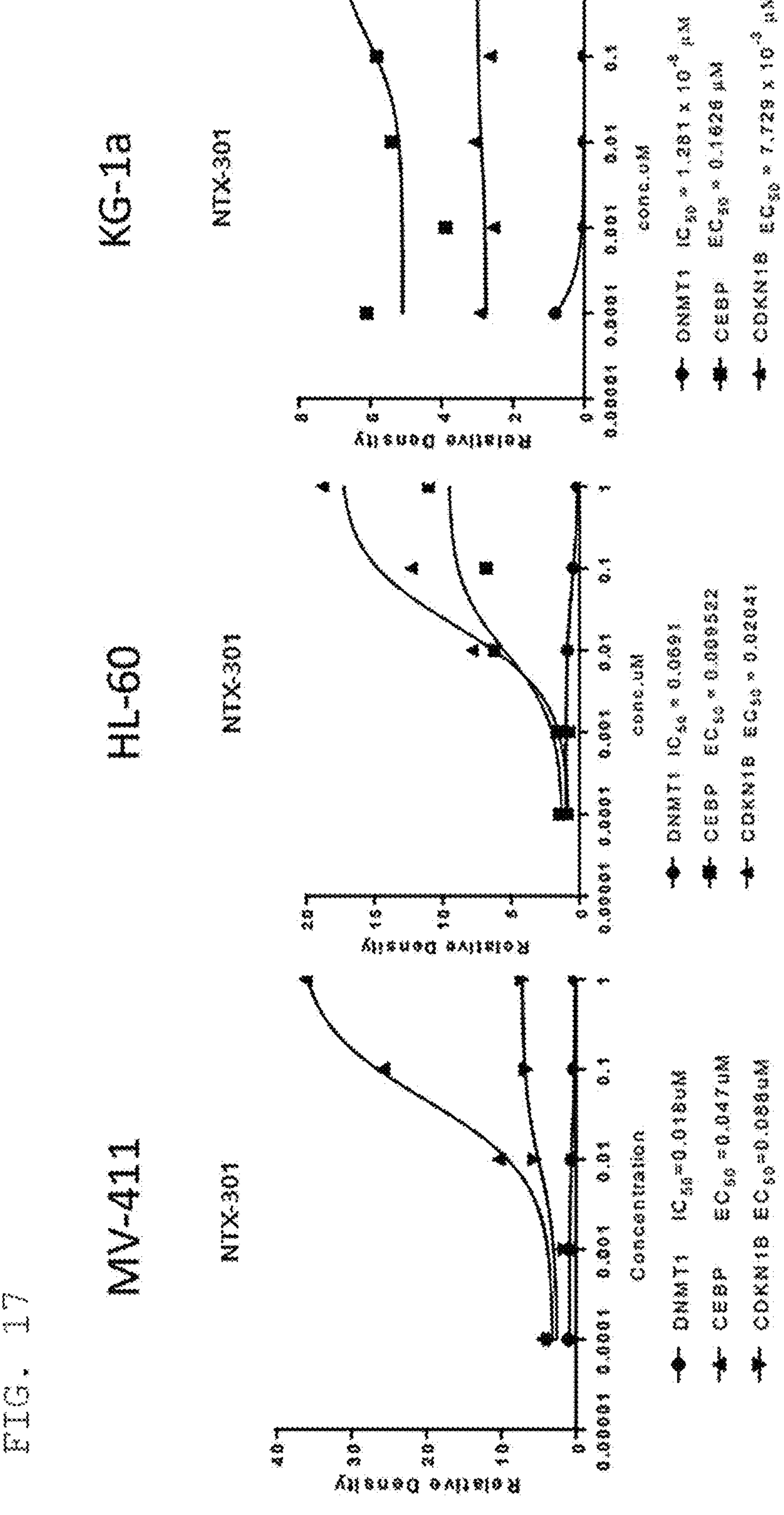
FIG. 17 shows the intracellular DNMT1, CEBP/epsilon, and CDKN1B levels of various AML cell lines (MV4-11, HL-60, KG-1a) treated with Aza-T-dCyd.

After treating AML cell lines MV4-11, HL-60, and KG-1a cells with Aza-T-dCyd (NTX-301) for 72 hours, we checked the intracellular protein expression levels and found that the expression of DNMT1 was inhibited and the expression of CEBP/epsilon and CDKN1B was increased. The greatest increase in expression was observed in MV4-11 and HL-60 cells (FIG. 17).

1-3. Target Engagement

Through previous experiments, we constructed a KO cell line in which DNMT1 knock-out (siRNA) treatment of MV4-11 cells, identified as a responsive cell line to Aza-T-dCyd, did not affect the survival, division, and growth of the cells.

Figure 18:
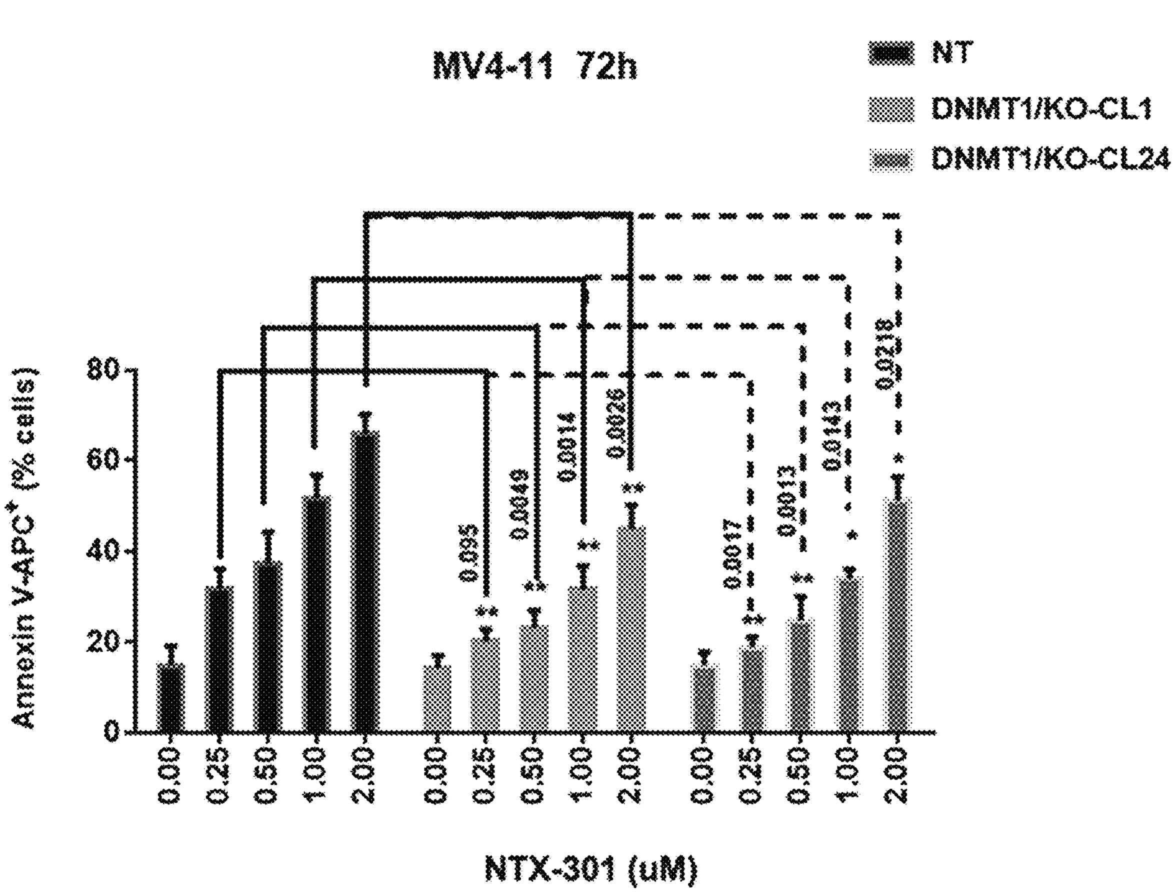
FIG. 18 shows the results of NTX-301 target engagement.

Treatment of the constructed DNMT1 knock-out cell line with Aza-T-dCyd (NTX-301) in a concentration-dependent manner resulted in a decrease in cytotoxicity, which was thought to be the result of attenuated pharmacological action on MV4-11 cells. This confirms that Aza-T-dCyd has potent pharmacological effects through DNMT1 (FIG. 18).

1-4. Cellular Cytotoxicity

The growth-inhibitory activity of Aza-T-dCyd, a DNMT1 inhibitor, was measured in leukemia cell lines to determine its inhibitory effect on cell proliferation.

1-4-1. AML

Figure 19:
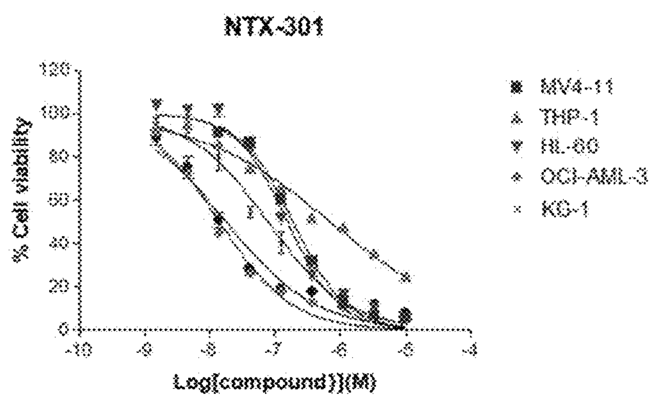
FIG. 19 is a plot showing the growth inhibitory effect of Aza-T-dCyd on blood cancer cell lines.

In various AML cell lines, Aza-T-dCyd (NTX-301) showed excellent cell viability inhibition with $IC_{50}$ values as shown in FIG. 19.

Figure 20:
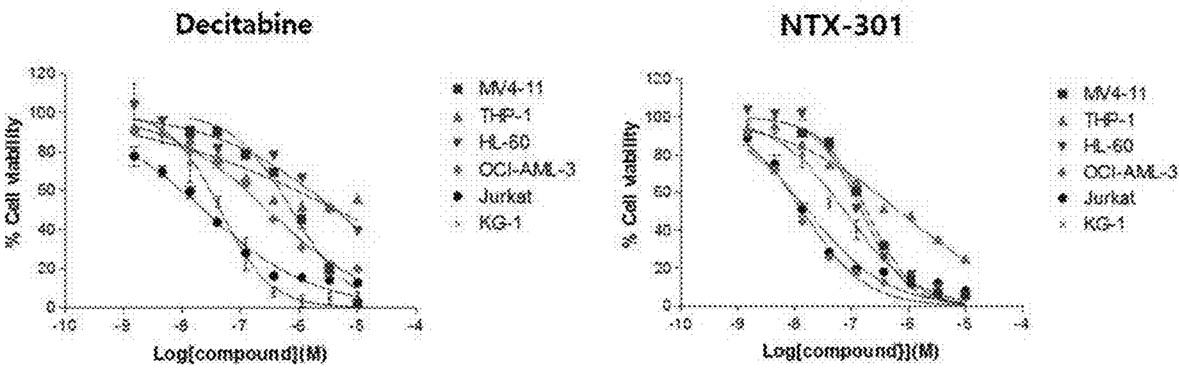
FIG. 20 is a plot comparing the growth inhibitory effects of Aza-T-dCyd and Decitabine on blood cancer cell lines.

1-4-2. Comparison of the Effects of DNMT1 Inhibitors on Cell Proliferation of Leukemia Cell Lines The growth-inhibitory activity of DNMT1 inhibitors, Aza-T-dCyd and Decitabine, was measured on leukemia cell lines to determine their effect on cell proliferation. After treating the DNMT1 inhibitors for 72 hours each, the GI50 values (half maximal growth inhibitory concentrations) of Decitabine, which is known to be effective in inhibiting leukemia cell growth, ranged from 0.024 μM to 4.3 μM, and the GI50 values of Aza-T-dCyd ranged from 0.014 μM to 0.69 μM. Overall, when comparing the inhibitory efficacy on cell proliferation, it was found that the efficacy of Aza-T-dCyd was significantly superior to that of Decitabine (FIG. 20).

1-4-3. Results of $IC_{50}$ Values of Aza-T-dCyd in Cancer Type-Specific Cell Lines To obtain a biomarker for Aza-T-dCyd, drug activity profiling analysis was performed to evaluate the cytotoxicity of 200 cell lines.

The drug responsiveness analysis of Aza-T-dCyd through drug activity profiling and genomic analysis of 200 cell lines confirmed the potent efficacy of Aza-T-dCyd in various solid tumors (Table 2).

TABLE 2

| cell lines | cancer type | Aza-T-dCyd $IC_{50}$ (uM) |
|---|---|---|
| NALM-6 | ALL | 0.0338 |
| RS4; 11 | ALL | 0.0203 |
| Jurkat | ALL | 0.0695 |
| MOLT-16 | ALL | 0.0182 |
| CCRFCEM | ALL | 0.119 |
| MOLT-4 | ALL | 0.035 |
| HL-60 | AML | 0.514 |
| KG-1 | AML | 0.461 |
| MV-4-11 | AML | 0.183 |
| Thp1 | AML | 5.12 |
| MC116 | B-cell lymphoma | 0.0297 |
| JeKo-1 | B-cell lymphoma | 0.0385 |
| DB | B-cell lymphoma | 0.135 |
| DOHH-2 | B-cell lymphoma | 0.609 |
| HT | B-cell lymphoma | 1.03 |
| NU-DUL-1 | B-cell lymphoma | 0.0245 |
| SU-DHL-10 | B-cell lymphoma | 0.0366 |
| SU-DHL-4 | B-cell lymphoma | 0.0175 |
| SU-DHL-8 | B-cell lymphoma | 0.0706 |
| ARH-77 | B-cell lymphoma | 0.413 |
| BC-1 | B-cell lymphoma | 0.338 |
| IM-9 | B-cell lymphoma | 1.05 |
| MHH-PREB-1 | B-cell lymphoma | 0.0389 |

TABLE 2-continued

| cell lines | cancer type | Aza-T-dCyd $IC_{50}$ (uM) |
|---|---|---|
| RPMI 8226 | B-cell myeloma | 3.27 |
| SKO-007 | B-cell myeloma | 4.29 |
| CA46 | Burkitt's lymphoma | 0.0255 |
| Daudi | Burkitt's lymphoma | 0.451 |
| GA-10 | Burkitt's lymphoma | 0.0335 |
| NAMALWA | Burkitt's lymphoma | 0.0109 |
| Raji | Burkitt's lymphoma | 0.0752 |
| EB2 | Burkitt's lymphoma | 8.19 |
| MEG01 | CML | 1.07 |
| BV-173 | CML | 0.00532 |
| CML-T1 | CML | 0.109 |
| EM-2 | CML | 0.255 |
| TF-1 | Erythroleukemia | 0.733 |
| L-428 | Hodgkin's lymphoma | 0.365 |
| RPMI 6666 | Hodgkin's lymphoma | 1.05 |
| H9 | T-cell Lymphoma | 0.468 |
| J-RT3-T3-5 | T-cell Lymphoma | 0.106 |
| OE33 | Head and Neck | 0.161 |
| A-673 | Sarcoma | 0.698 |
| A375 | Skin (Melanoma) | 0.0667 |
| C32 | Skin (Melanoma) | >10 |
| H4 | CNS (Glioma) | 0.0801 |
| U-118 MG | CNS (Glioma) | >10 |
| 5637 | Bladder | 0.296 |
| HT-1197 | Bladder | 7.13 |
| HT1376 | Bladder | 3.28 |
| J82 | Bladder | 1.98 |
| T24 | Bladder | 1.53 |
| TCCSUP | Bladder | 1.18 |
| UM-UC-3 | Bladder | 0.289 |
| SCaBER | Bladder | 0.187 |
| 647-V | Bladder | 0.408 |
| BFTC-905 | Bladder | 0.119 |
| Hs 821.T | Sarcoma | >10 |
| AU565 | Breast | >10 |
| CAMA-1 | Breast | >10 |
| MDA MB 231 | Breast | 0.21 |
| MDA MB 415 | Breast | >10 |
| MDA MB 453 | Breast | 1.89 |
| MDA MB 468 | Breast | 1.34 |
| SK-BR-3 | Breast | 9.32 |
| EFM-19 | Breast | 3.95 |
| ChaGoK1 | Lung (NSCLC) | 3.41 |
| LS1034 | Colon | 1.41 |
| LS411N | Colon | 0.265 |
| NCI-H508 | Colon | 0.542 |
| NCI-H747 | Colon | 0.319 |
| Caki-1 | Kidney | 0.0856 |
| HCT-15 | Colon | 1.02 |
| SW1417 | Colon | >10 |
| SW403 | Colon | 0.619 |
| SW480 | Colon | 1.58 |
| SW620 | Colon | 0.234 |
| HCT-116 | Colon | 0.1 |
| SK-MEL-28 | Skin (Melanoma) | 2.5 |
| Daoy | CNS (Medulloblastoma) | 3.61 |
| A204 | Sarcoma | 0.157 |
| Hs 729 | Sarcoma | >10 |
| RL95-2 | Female GU (Uterus) | 0.705 |
| OE19 | Head and Neck | >10 |
| OE21 | Head and Neck | 0.152 |
| HT-1080 | Sarcoma | 0.12 |
| AGS | Stomach | 0.0584 |
| Hs 746T | Stomach | 0.666 |
| A172 | CNS (Glioma) | >10 |
| DBTRG-05MG | CNS (Glioma) | >10 |
| DK-MG | CNS (Glioma) | >10 |
| T98G | CNS (Glioma) | 1.39 |
| U-87 MG | CNS (Glioma) | 1.64 |
| HepG2 | Liver | 0.892 |
| OVCAR3 | Female GU (Ovary) | 3.44 |
| FaDu | Head and Neck | 0.208 |
| HuCCT1 | Liver | 0.105 |
| BT20 | Breast | >10 |
| BT474 | Breast | >10 |
| Hs 578T | Breast | >10 |
| MCF7 | Breast | 6.47 |
| ZR-75-1 | Breast | >10 |

TABLE 2-continued

| cell lines | cancer type | Aza-T-dCyd $IC_{50}$ (uM) |
|---|---|---|
| COR-L23 | Lung (NSCLC) | 0.0944 |
| A549 | Lung (NSCLC) | 0.19 |
| COR-L105 | Lung (NSCLC) | 2.24 |
| D283 Med | CNS (Medulloblastoma) | 0.0688 |
| G-361 | Skin (Melanoma) | 1.08 |
| Hs 688(A).T | Skin (Melanoma) | >10 |
| Hs 852.T | Skin (Melanoma) | >10 |
| MALME3M | Skin (Melanoma) | 7.45 |
| MeWo | Skin (Melanoma) | 1.04 |
| RPMI-7951 | Skin (Melanoma) | 0.527 |
| SH-4 | Skin (Melanoma) | 0.698 |
| SK-MEL-3 | Skin (Melanoma) | 0.522 |
| WM-266-4 | Skin (Melanoma) | 0.429 |
| TT | Endocrine (Thyroid) | >10 |
| SK-N-AS | CNS (Neuroblastoma) | 1.17 |
| SK-N-FI | CNS (Neuroblastoma) | 2.71 |
| MG-63 | Bone (Osteosarcoma) | 0.99 |
| SKOV3 | Female GU (Ovary) | 2.92 |
| HuP-T4 | Pancreas | 0.321 |
| Hs 766T | Pancreas | 9.4 |
| PSN-1 | Pancreas | 0.191 |
| YAPC | Pancreas | 1.05 |
| AsPC-1 | Pancreas | 2.12 |
| BxPC-3 | Pancreas | 0.699 |
| CFPAC-1 | Pancreas | 1.75 |
| Capan-1 | Pancreas | 3.32 |
| HPAF-II | Pancreas | 0.737 |
| Mia PaCa-2 | Pancreas | 0.881 |
| NCIH441 | Lung (NSCLC) | 1.3 |
| ACHN | Kidney | 0.231 |
| Caki-2 | Kidney | 0.363 |
| Detroit 562 | Head and Neck | 0.0811 |
| 22Rv1 | Prostate | 2.71 |
| DU145 | Prostate | 0.432 |
| PC-3 | Prostate | 0.441 |
| NCI-H292 | Lung (NSCLC) | 0.194 |
| SW1463 | Colon | 0.303 |
| SW837 | Colon | 0.354 |
| HT-29 | Colon | 0.323 |
| 769-P | Kidney | 0.0657 |
| 786-O | Kidney | 0.249 |
| A498 | Kidney | 0.0738 |
| A-704 | Kidney | >10 |
| A-253 | Head and Neck | 0.601 |
| KATO III | Stomach | 0.807 |
| DMS114 | Lung (SCLC) | 2.2 |
| DMS273 | Lung (SCLC) | 5.66 |
| DMS53 | Lung (SCLC) | 4.22 |
| NCIH446 | Lung (SCLC) | 3.04 |
| NCI-H69 | Lung (SCLC) | >10 |
| SKMES1 | Lung (NSCLC) | 0.314 |
| SW579 | Endocrine (Thyroid) | 1.05 |
| BHT-101 | Endocrine (Thyroid) | 0.235 |
| Cal 27 | Head and Neck | 0.319 |
| SCC-25 | Head and Neck | 0.126 |
| SCC-4 | Head and Neck | 2.86 |
| SCC-9 | Head and Neck | 1.83 |
| Calu6 | Lung (NSCLC) | 0.289 |
| 639-V | Bladder | 1.57 |
| SK-UT-1 | Sarcoma | 0.343 |
| MES-SA | Sarcoma | 0.135 |
| A388 | Skin (Head and Neck) | 0.19 |
| A427 | Lung (NSCLC) | 0.0775 |
| A431 | Skin (Head and Neck) | 0.256 |
| A7 | Skin (Melanoma) | 1.19 |
| BE(2)C | CNS (Neuroblastoma) | 0.373 |
| BM-1604 | Prostate | 4.41 |
| C32TG | Skin (Melanoma) | 0.953 |
| C-33A | Female GU (Cervix) | 0.497 |
| C-4 II | Female GU (Cervix) | 0.773 |
| CGTH-W-1 | Endocrine (Thyroid) | 0.143 |
| Colo 205 | Colon | 0.0811 |
| Colo 320DM | Colon | 0.0923 |
| DLD-1 | Colon | 0.221 |
| HeLa | Female GU (Cervix) | 1.81 |
| Hs 936.T(C1) | Skin (Melanoma) | 0.398 |
| HT-3 | Female GU (Cervix) | 0.818 |
| JAR | Placenta | 0.296 |
| KHOS-240S | Bone (Osteosarcoma) | 0.254 |
| LS-174T | Colon | >10 |
| MS751 | Female GU (Cervix) | >10 |
| NCI-H295R | Endocrine (Adrenal gland) | >10 |
| NTERA-2 cl.D1 | Testis | 0.0427 |
| PA-1 | Female GU (Ovary) | 0.0392 |
| PFSK-1 | CNS (Glioma) | 7.61 |
| SJRH30 | Sarcoma | 0.291 |
| SK-NEP-1 | Kidney | >10 |
| SK-PN-DW | Sarcoma | 0.847 |
| SNB-19 | CNS (Glioma) | 0.17 |
| SU.86.86 | Pancreas | 0.508 |
| SW872 | Sarcoma | 0.73 |
| SW900 | Lung (SCLC) | 1.98 |
| SW962 | Female GU (Vulva) | >10 |
| SW982 | Sarcoma | 0.171 |
| T47D | Breast | >10 |
| U-138MG | CNS (Glioma) | >10 |
| VA-ES-BJ | Sarcoma | 0.241 |
| WiDr | Colon | 0.263 |
| D341 Med | CNS (Medulloblastoma) | NA |

Example 2: Studying the Mechanism of Action of Aza-T-dCyd

Figure 1:
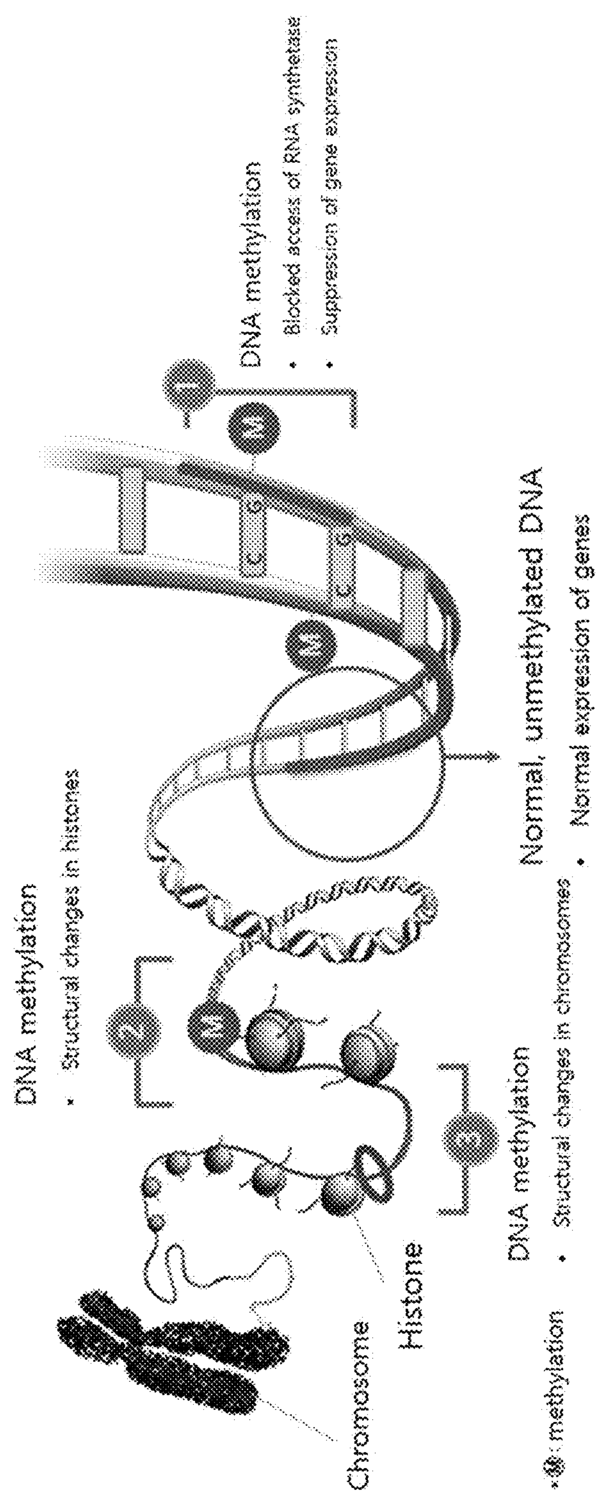
FIG. 1 is a schematic representation of the epigenetic mechanism of action.
Figure 2:
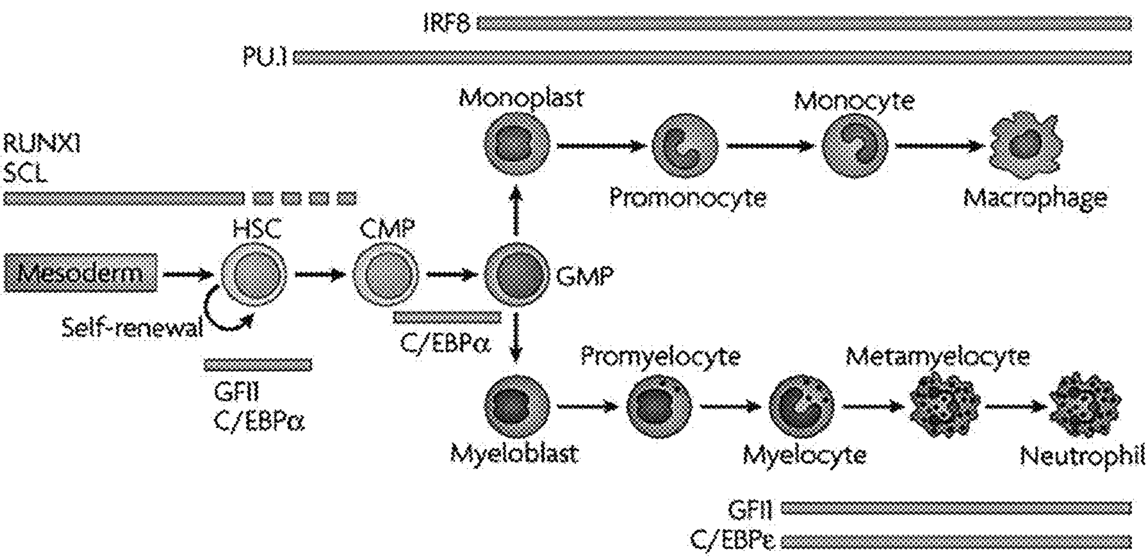
FIG. 2 is a schematic representation of the normal hematopoiesis process in the body. The role of master TFs (especially CEBP/epsilon) in driving each phase is crucial: phase 1, where rapid cell division ensures cell number, and phase 2, where cell division stops and cell maturation occurs.
Figure 3:
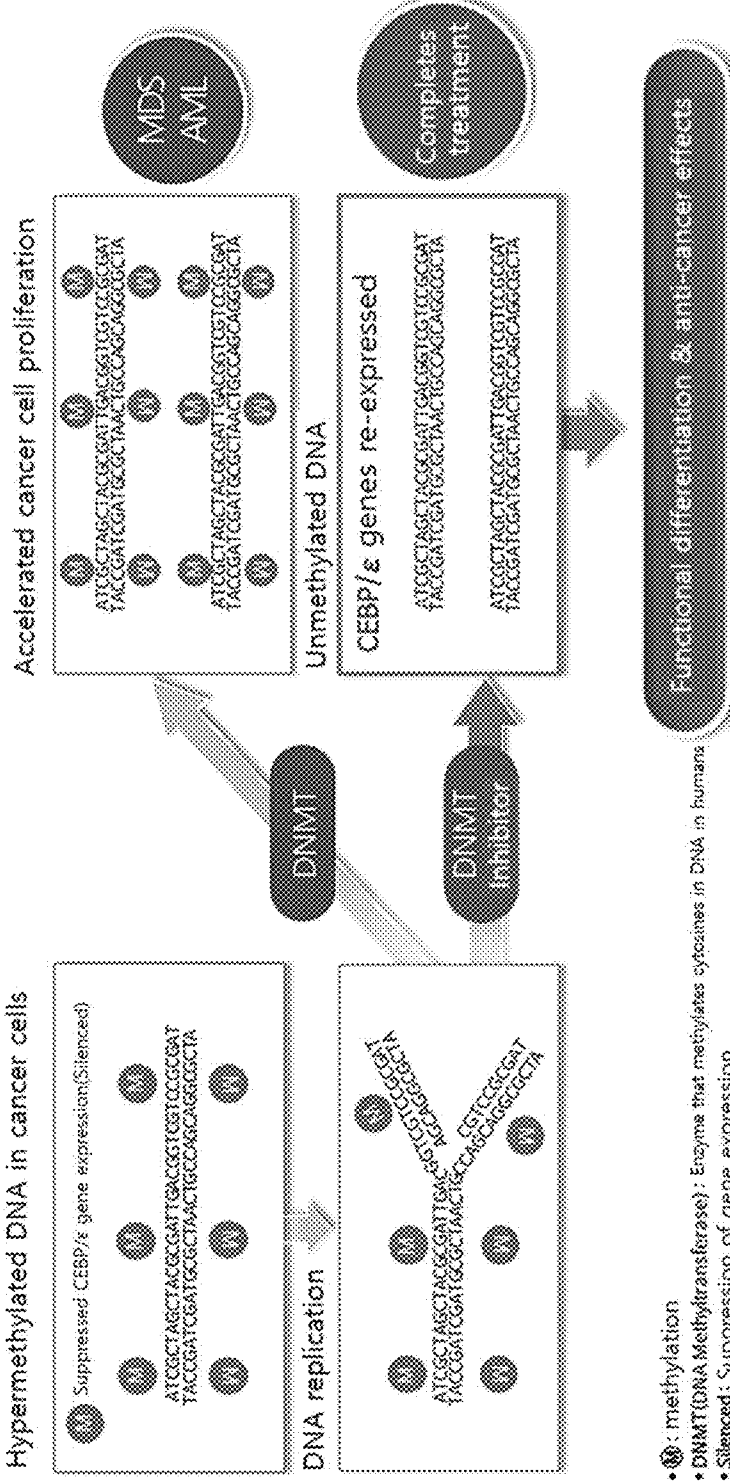
FIG. 3 is a schematic illustrating that DNMT inhibitor treatment induced normal DNA methylation in hypermethylated MDS/AML blood cancer cells, leading to differentiation into normal cells through re-expression of the CEBP/epsilon gene and exerting anticancer effects.
Figure 4:
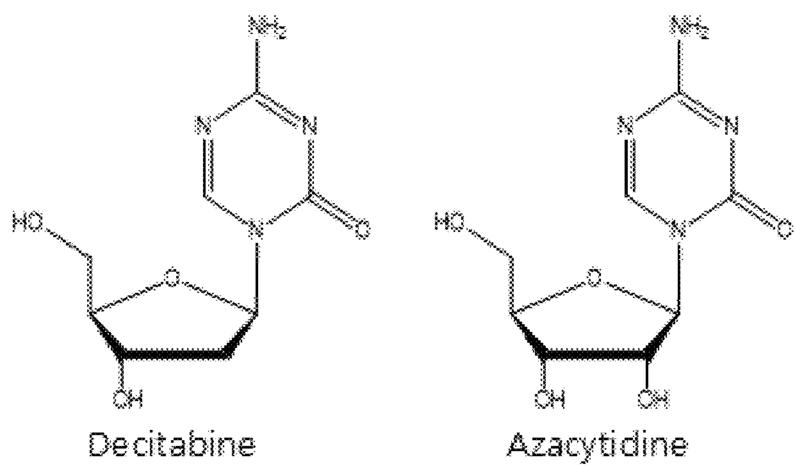
FIG. 4 is the chemical structure of Decitabine and Azacytidine.
Figure 5:
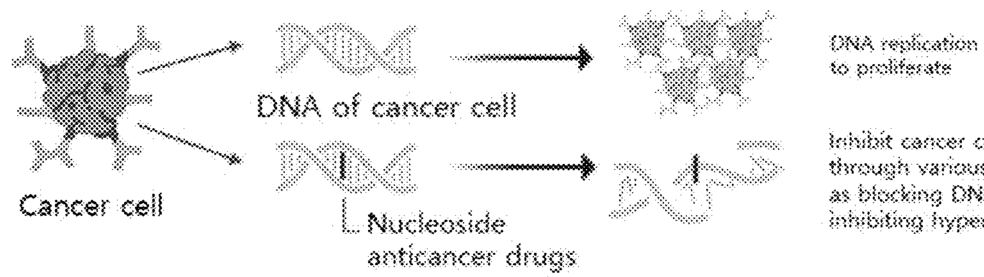
FIG. 5 is the mechanism of action of nucleoside-based anticancer drugs.
Figure 6:
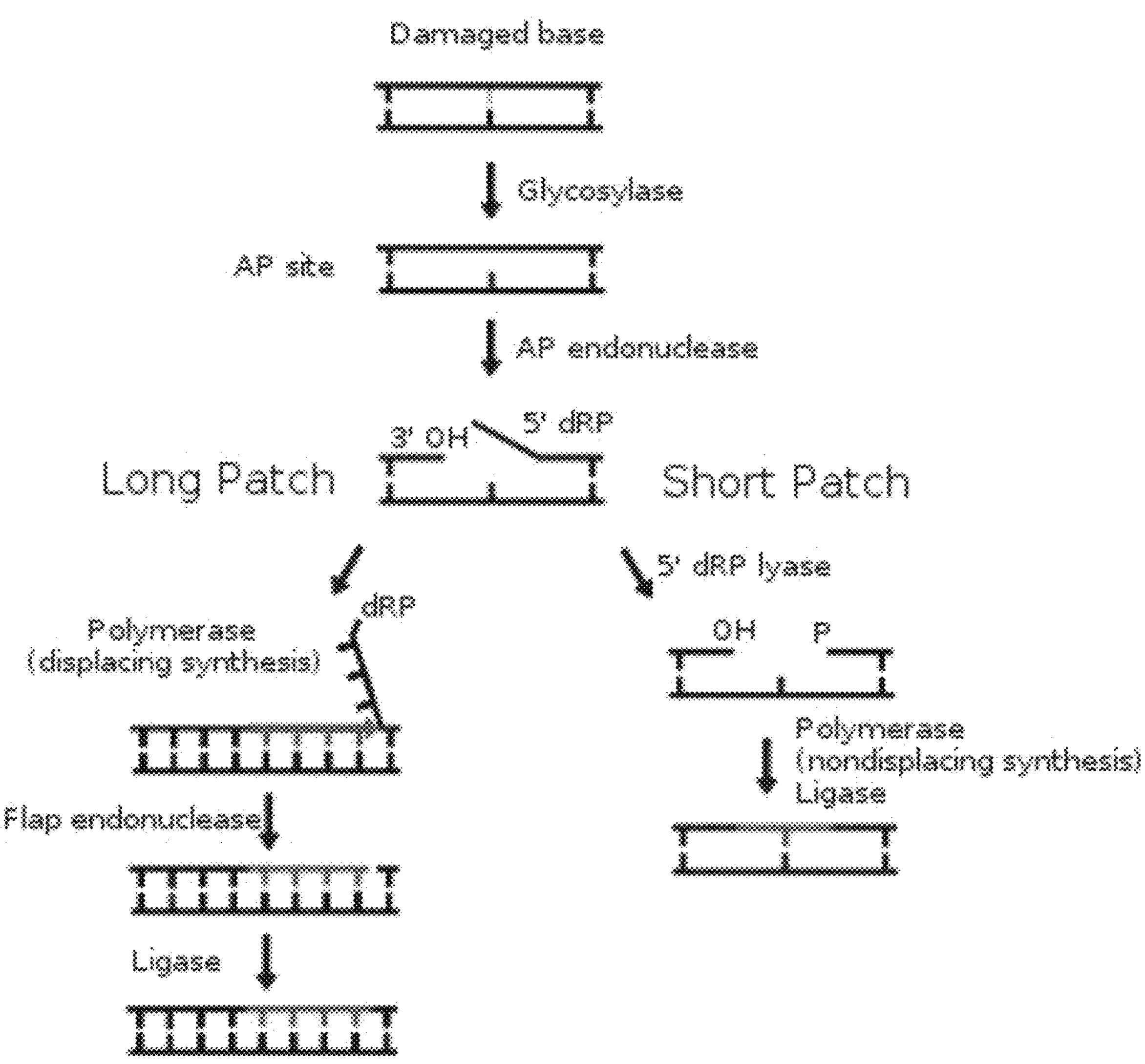
FIG. 6 is the DNA damage repair process of nucleoside-based anticancer drugs by BER mechanism.
Figure 7:
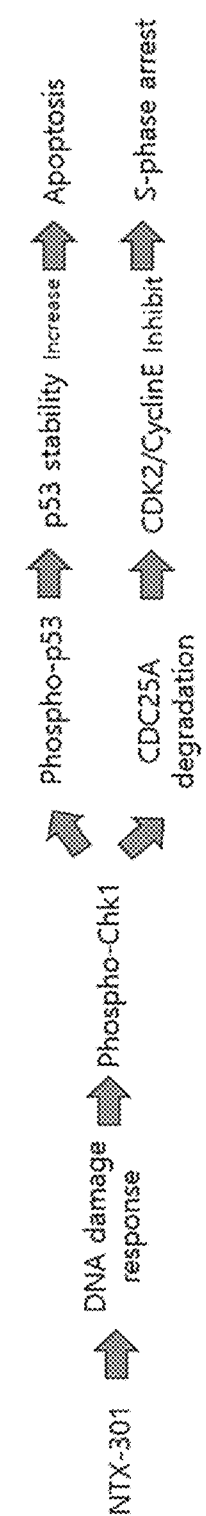
FIG. 7 is the mechanism of action of Aza-T-dCyd to mediate apoptosis and cell cycle arrest through DNA damage response.
Figure 8:
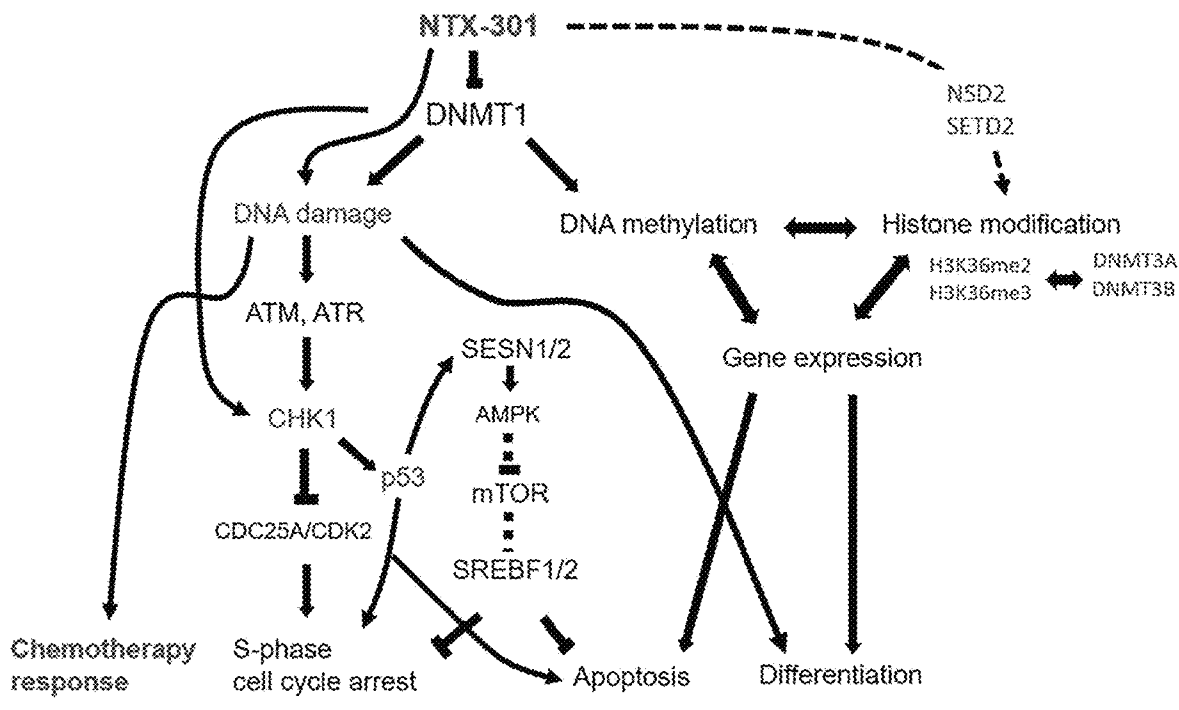
FIG. 8 is the mechanism of action of Aza-T-dCyd.
Figure 9:
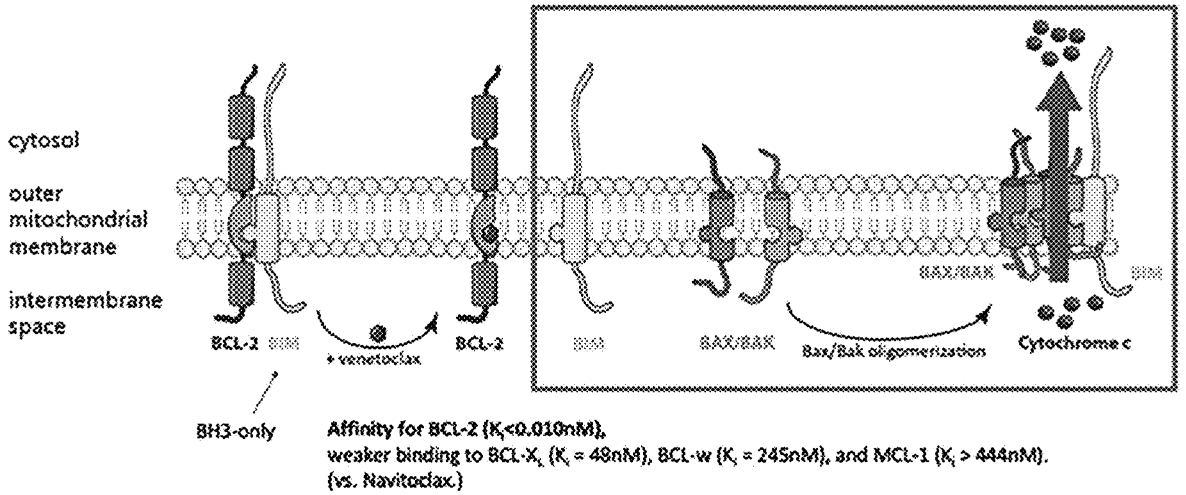
FIG. 9 illustrates the mechanism of action of B-cell lymphoma (BCL)-2 and its inhibitor, venetoclax, in mediating apoptosis.
Figure 9:
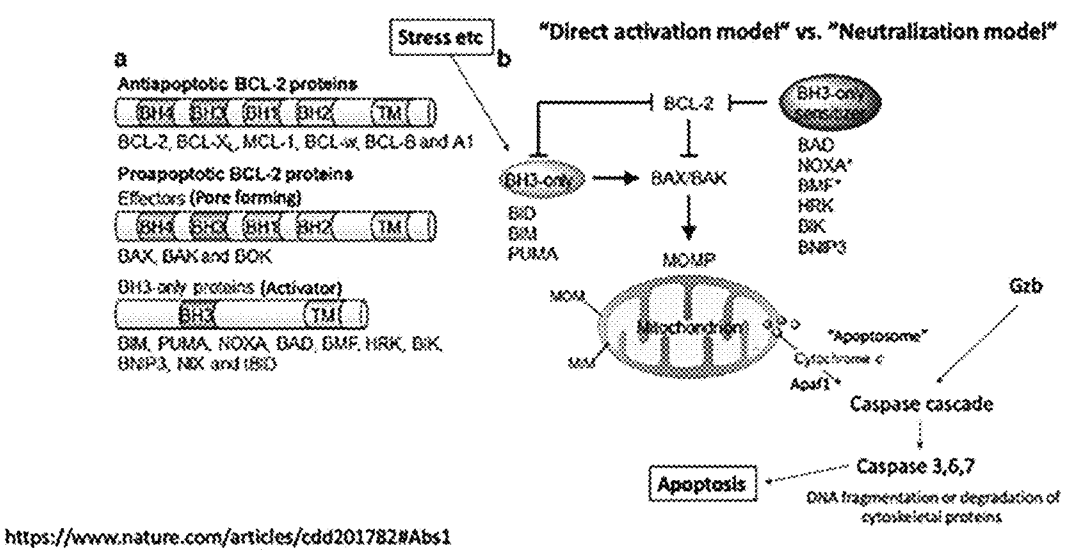

FIGS. 7 and 8 illustrate the mechanism of action of Aza-T-dCyd in DNA damage response and the mechanism of action of Aza-T-dCyd, respectively.

By DNA incorporation and DNMT1 trapping through the azacytosine functional group, which can well trap DNMT1 enzyme, Aza-T-dCyd forms a longer-lasting DNA-DNMT1 adduct compared to Decitabine, inducing stronger DNA damage and strongly activating the CHK1-p53 pathway, which shows stronger anticancer efficacy compared to Decitabine.

2-1. Induction of DNA Damage Response

①DNA Incorporation and Inhibition of Pyrimidine Metabolism

Aza-T-dCyd is a pyrimidine analog and is metabolized by various pyrimidine metabolism-related enzymes in cells.

Figure 21:
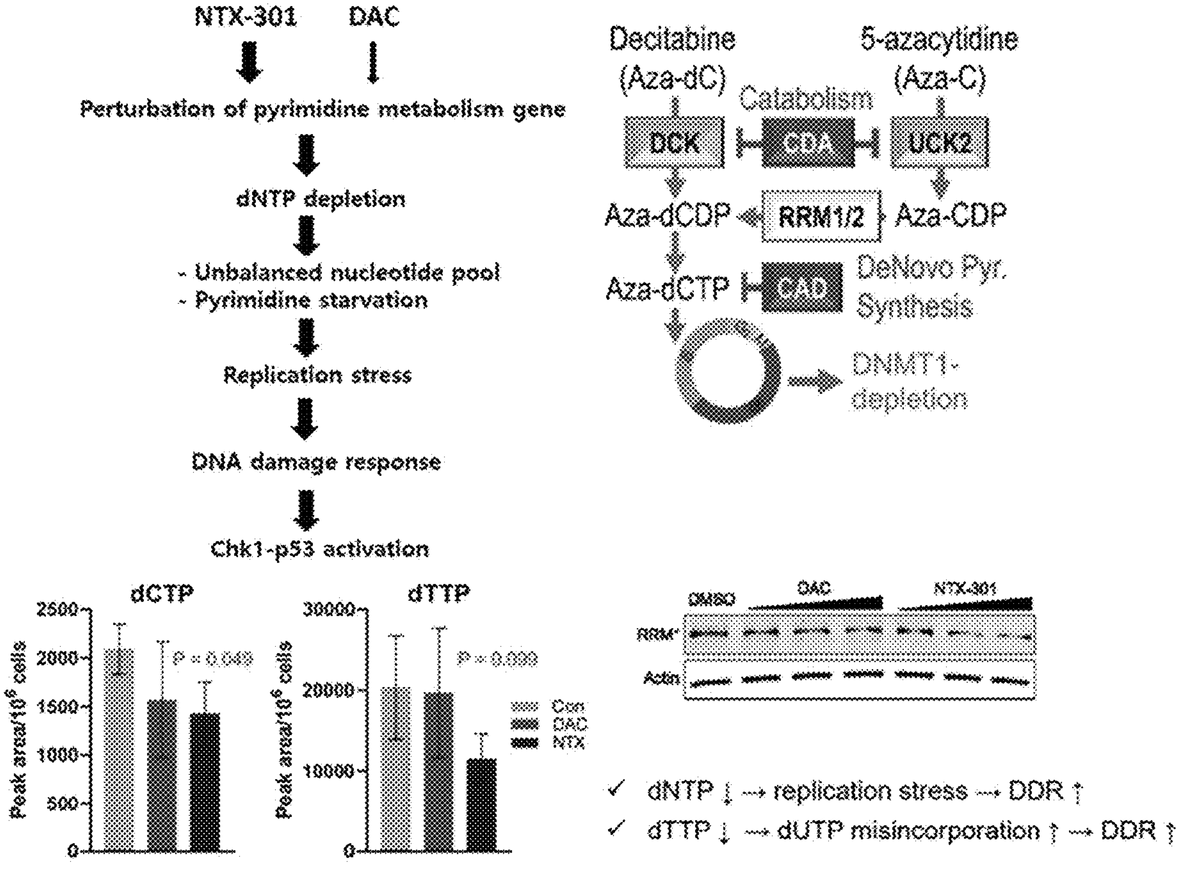
FIG. 21 is a plot of pyrimidine level and RRM1 expression upon NTX-301 treatment.

Treatment of cells with Aza-T-dCyd (NTX-301) inhibited the expression of RRM1 protein, a ribonucleotide reductase important for dNTP de novo synthesis, and decreased the amount of dCTP and dTTP in the cells, indicating that it may affect the intracellular pyrimidine metabolism process (FIG. 21). The reduction of dCTP and dTTP, which act as important precursors for cancer cells to replicate DNA, can cause replication stress and generate a strong DNA damage response.

DNA insertion of aza-T-dCTP, a metabolite of Aza-T-dCyd, can cause base excision repair, mismatch repair, and delay DNA replication, thereby inducing replication stress and exacerbating the DNA damage response.

②Induction of DNA Damage Response Through Formation of DNA-DNMT1 Adducts

Upon Aza-T-dCyd treatment, Aza-T-dCyd inserted into intracellular DNA is trapped through covalent binding with DNMT1 and forms a DNA-DNMT1 adduct.

The formed adduct can interfere with the progression of the DNA replication fork through its bulky structure, causing the replication fork to collapse, causing double-strand breaks and triggering a strong DNA damage response.

Pyrimidine metabolism, DNA incorporation, and DNMT1 adduct formation result in a strong DNA damage response.

Figure 22:
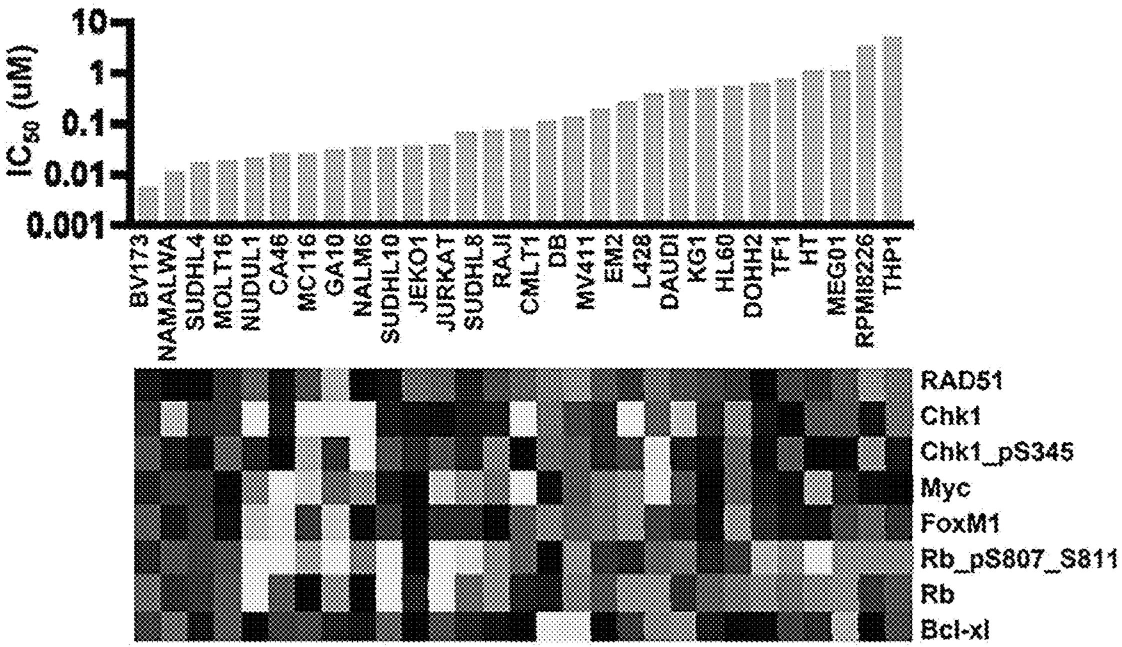
FIG. 22 shows the increased expression of DNA replication stress-related genes due to DNA adducts formed upon NTX-301 treatment, and the efficacy of the drug against each cell line.
Figure 22:
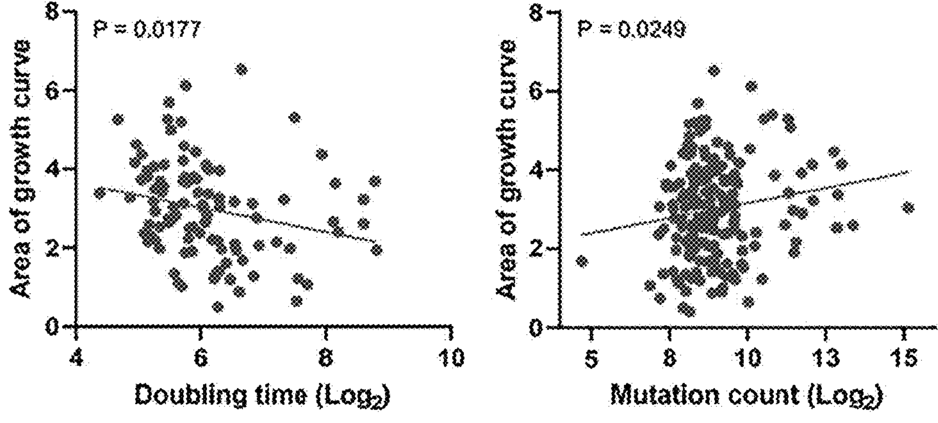

In FIG. 22, DNA adducts formed upon Aza-T-dCyd treatment resulted in increased expression of DNA replication stress-related genes and cell line-specific drug responses.

③ Promotes DNA Damage Response Through Activation of DDR-p53 Pathway

Figure 23:
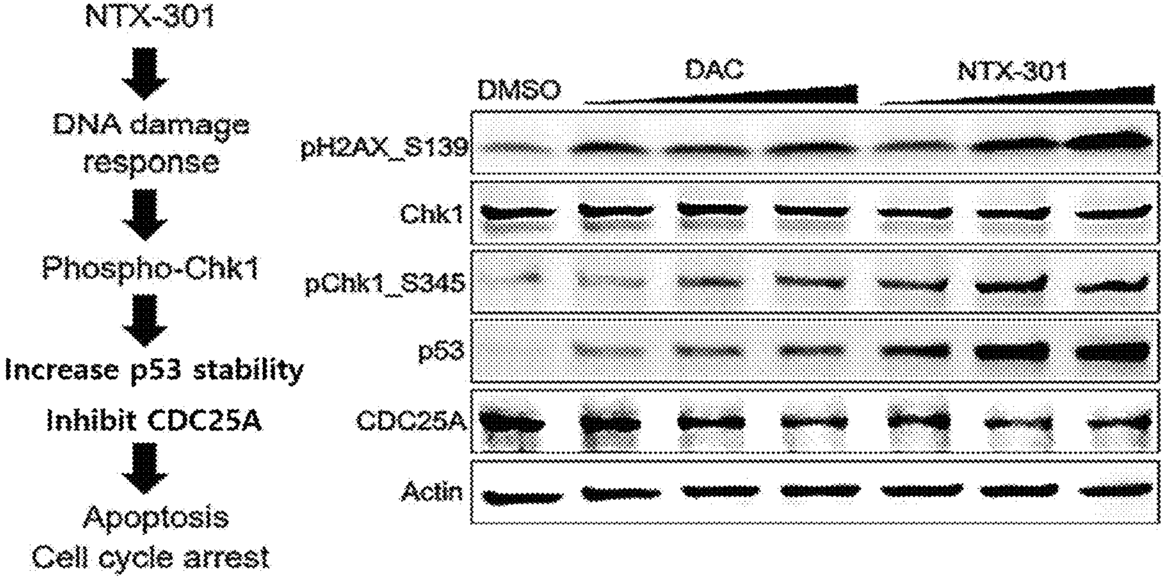
FIG. 23 shows increased DNA damage response markers due to p53 pathway activation upon NTX-301 treatment.
Figure 23:
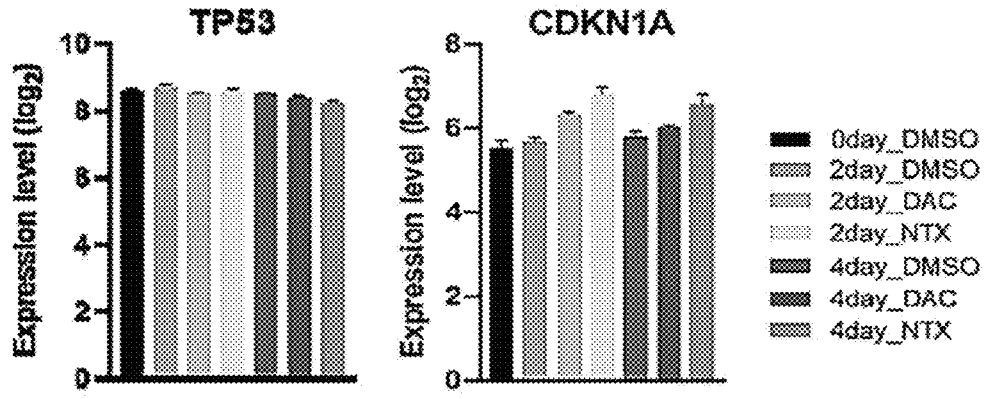

Aza-T-dCyd (NTX-301) treatment increased H2AX phosphorylation, a DNA damage response marker, and simultaneously increased phosphorylation of Chk1, a DNA damage sensor, and increased expression of p53 protein, which regulates cell cycle/apoptosis in the DNA damage response, thereby promoting the DNA damage response and consequently inhibiting the tumorigenic activity of blood cancers (FIG. 23).

2-2. DNA Demethylation

Treatment with Aza-T-dCyd induces strong DNMT1 depletion and causes a decrease in overall DNA methylation levels.

While Decitabine induces genome-wide demethylation, Aza-T-dCyd induces biased and selective demethylation to DNA regions that are replicated during early replication, promoter regions important for gene expression, DNMT1-binding regions, and replication stress regions.

Figure 24:
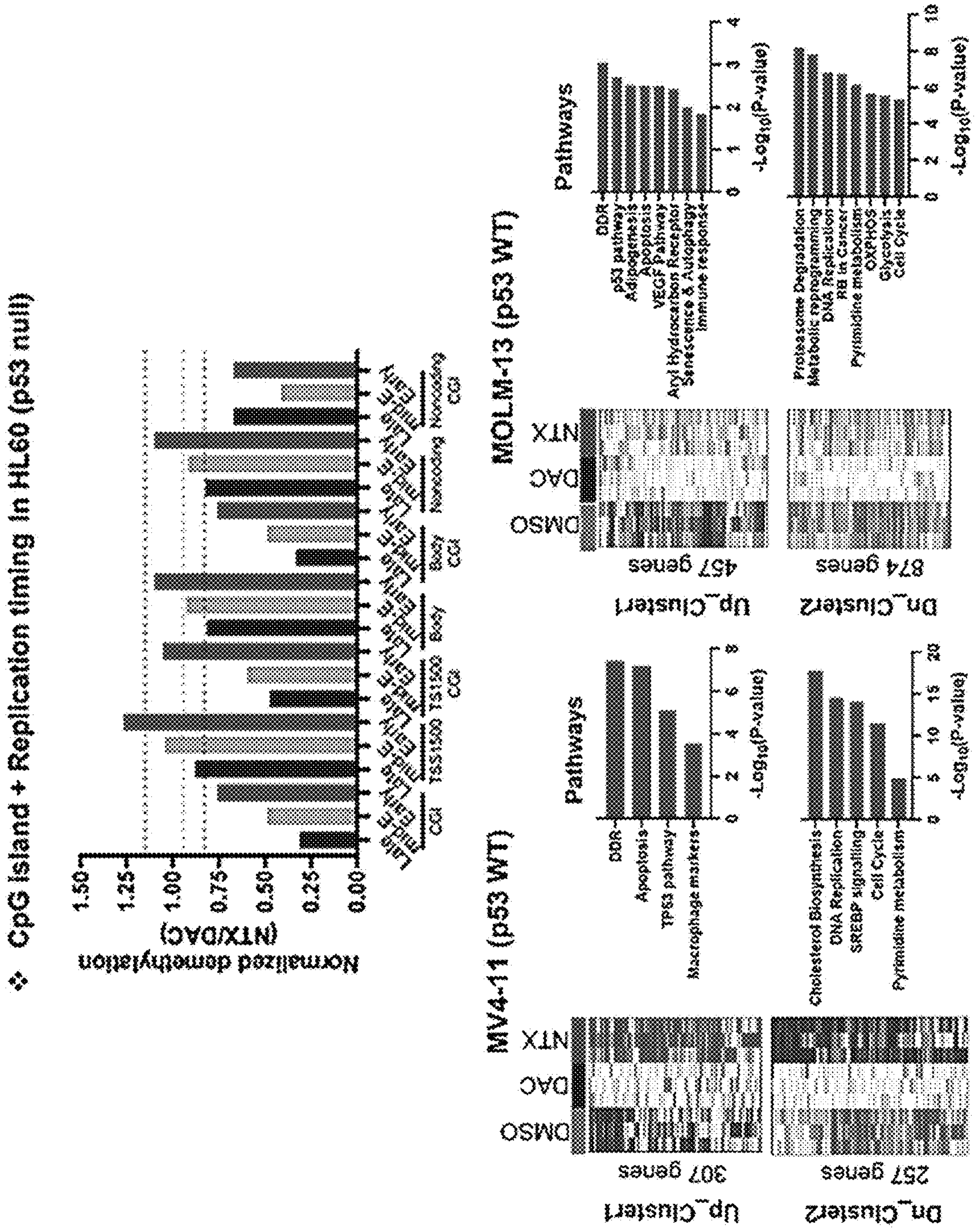
FIG. 24 shows selective DNA dimethylation induced by NTX-301 treatment of MV4-11 and MOLM-13 cell lines and analysis of RNA-seq data.

Through DNA demethylation caused by Aza-T-dCyd treatment, various tumor suppressor genes and genes required for differentiation induction of AML cells were reactivated, and the reactivated expression patterns of these genes were confirmed by RNA-seq data analysis (FIG. 24).

Example 3: Concentration-Specific Pharmacokinetic Evaluation-Mice/Rat/Dog PK Profile Aza-T-dCyd was administered orally and intravenously at various concentrations to Mice, Rats and Dogs to determine the PK profile.

The animal species that most closely resembles the actual distribution of the drug in humans is mice (which have the most similar metabolic pattern due to the predominant distribution of CDA (Cytidine Deaminase) in the liver as in humans). However, the PK profile in Rat/Dog was checked to ensure that the absorption was not different between species. We found that Aza-T-dCyd is orally bioavailable in mice, rats, and dogs, and that the $C_{max}$/AUC values in mice can be easily obtained at a level to ensure good drug efficacy, i.e., oral administration of Aza-T-dCyd above 0.5 mpk can easily achieve drug efficacy in vivo.

Table 3 and Table 4 show the results of pharmacokinetic evaluation of Aza-T-dCyd in Mice, Table 5 shows the results of pharmacokinetic evaluation of Aza-T-dCyd in Rat, and Table 6 shows the results of pharmacokinetic evaluation of Aza-T-dCyd in Dog.

TABLE 3

| | Dose (mg/kg) | | | | |
|---|---|---|---|---|---|
| Parameters | IV 1 | PO 0.5 | PO 1 | PO 3 | PO 10 |
| Tmax (h) | 0.083 | 0.300 | 0.300 | 0.450 | 0.450 |
| Cmax (ng/mL) | 341 | 51.8 | 103 | 576 | 1930 |
| T½ (h) | 0.503 | 0.701 | 0.628 | 0.824 | 1.11 |
| AUCt (ng*h/mL) | 257 | 62.4 | 106 | 919 | 2585 |
| AUC∞ (ng*h/mL) | 269 | 68.5 | 112 | 931 | 2596 |

TABLE 4

| | Dose (mg/kg) | | | | |
|---|---|---|---|---|---|
| Parameters | IV 1 | PO 0.5 | PO 1 | PO 3 | PO 10 |
| Tmax (h) | NA | 0.500 | 0.250 | 0.250 | 0.333 |
| Cmax (ng/mL) | 527 | 211 | 138 | 256 | 863 |
| T½ (h) | 0.612 | 0.304 | 1.72 | 1.11 | 1.15 |
| AUCt (ng*h/mL) | 370 | 118 | 136 | 303 | 1340 |
| AUC∞ (ng*h/mL) | 406 | 131 | 235 | 443 | 1465 |

TABLE 5

| | Dose (mg/kg) | | | | |
|---|---|---|---|---|---|
| Parameters | IV 1 | PO 0.5 | PO 1 | PO 3 | PO 10 |
| Tmax (h) | NA | 2.00 | 1.17 | 0.830 | 2.00 |
| Cmax (ng/mL) | 444 | 33.8 | 81.9 | 488 | 1323 |
| T½ (h) | 5.01 | 5.24 | 6.30 | 3.45 | 2.95 |
| AUCt (ng*h/mL) | 1332 | 190 | 459 | 2780 | 9199 |
| AUC∞ (ng*h/mL) | 1900 | 303 | 790 | 2801 | 9235 |

TABLE 6

| | Dose (mg/kg) | | | | | |
|---|---|---|---|---|---|---|
| Parameters | IV 0.33 | PO 0.15 | PO 0.33 | PO 0.67 | PO 1.5 | PO 3.0 |
| Tmax (h) | NA | 1.00 | 0.670 | 0.830 | 0.670 | 0.417 |
| Cmax (ng/mL) | 552 | 104 | 210 | 463 | 882 | 1673 |
| T½ (h) | 2.25 | 1.86 | 2.34 | 2.26 | 1.68 | 1.65 |
| AUCt (ng*h/mL) | 1046 | 409 | 790 | 1567 | 3205 | 5378 |
| AUC∞ (ng*h/mL) | 1128 | 439 | 880 | 1757 | 3372 | 5615 |

Based on these results, the predicted dose for efficacy in humans is 32 mg/day or less when administered alone and 8-16 mg/day when administered in combination, which falls within the range of the MTD in the Phase 1 study described below.

Example 4: In Vivo Pharmacology (PK/PD Correlation)

4-1. MDS/AML

Figure 25:
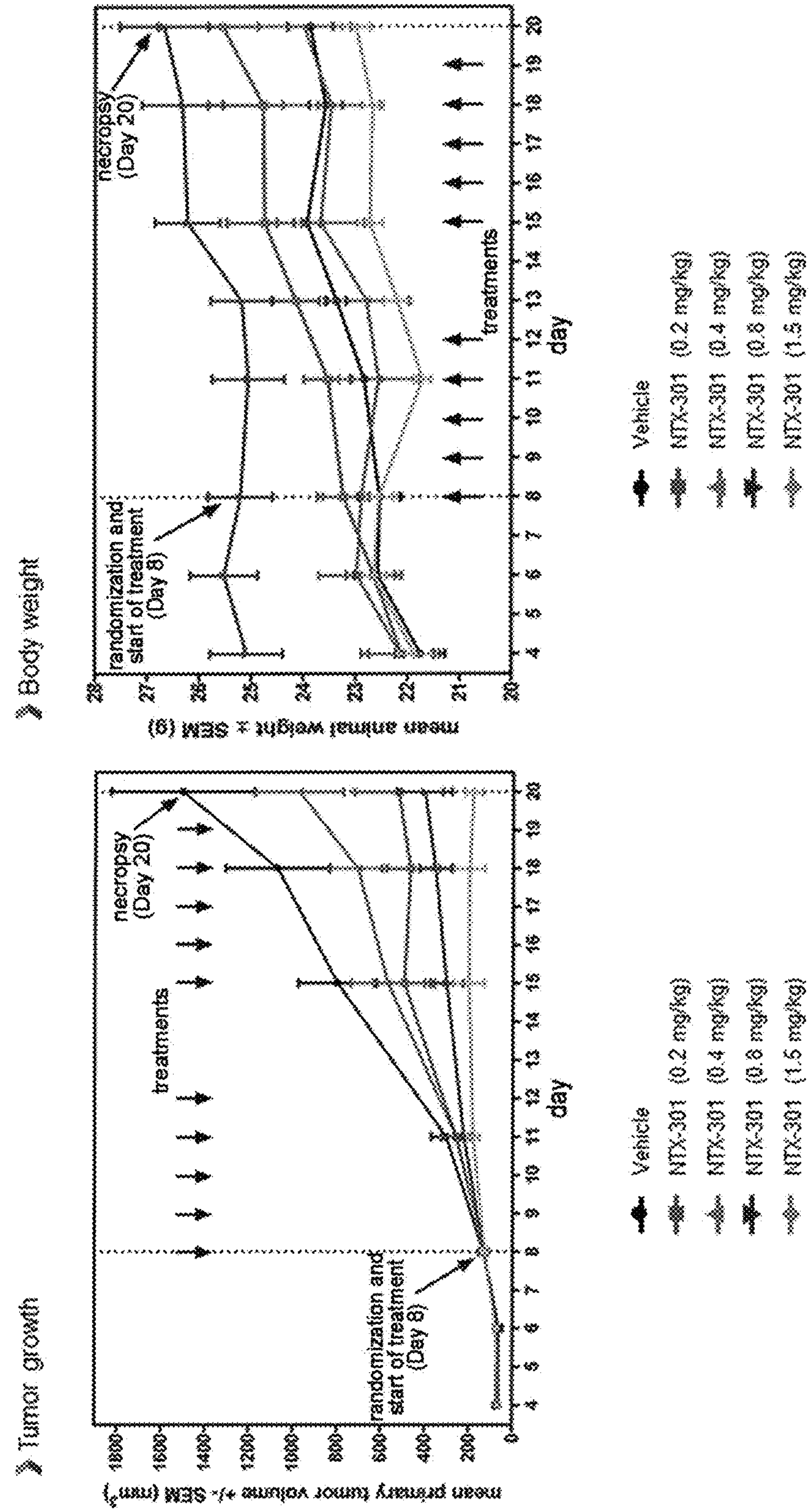
FIG. 25 shows a comparison of tumor growth and weight differences for each treatment group in the Molm13 leukemia cell line xenograft model.

To confirm the efficacy of Aza-T-dCyd in an animal model, and to confirm that Aza-T-dCyd exhibits superior pharmacological activity in a dose-dependent manner, a Molm13 Xenograft model experiment was performed (FIG. 25).

After establishing the Molm13 Xenograft model, an animal model of AML in which decitabine/azacytidine has no therapeutic effect, Aza-T-dCyd (NTX-301) was administered orally at doses of 0.2-1.5 mg/kg.

The administration of Aza-T-dCyd was found to have a potent anti-cancer effect in a dose-dependent manner without any toxicity signals (body weight changes), unlike the existing literature on Decitabine/Azacytidine.

Figure 26:
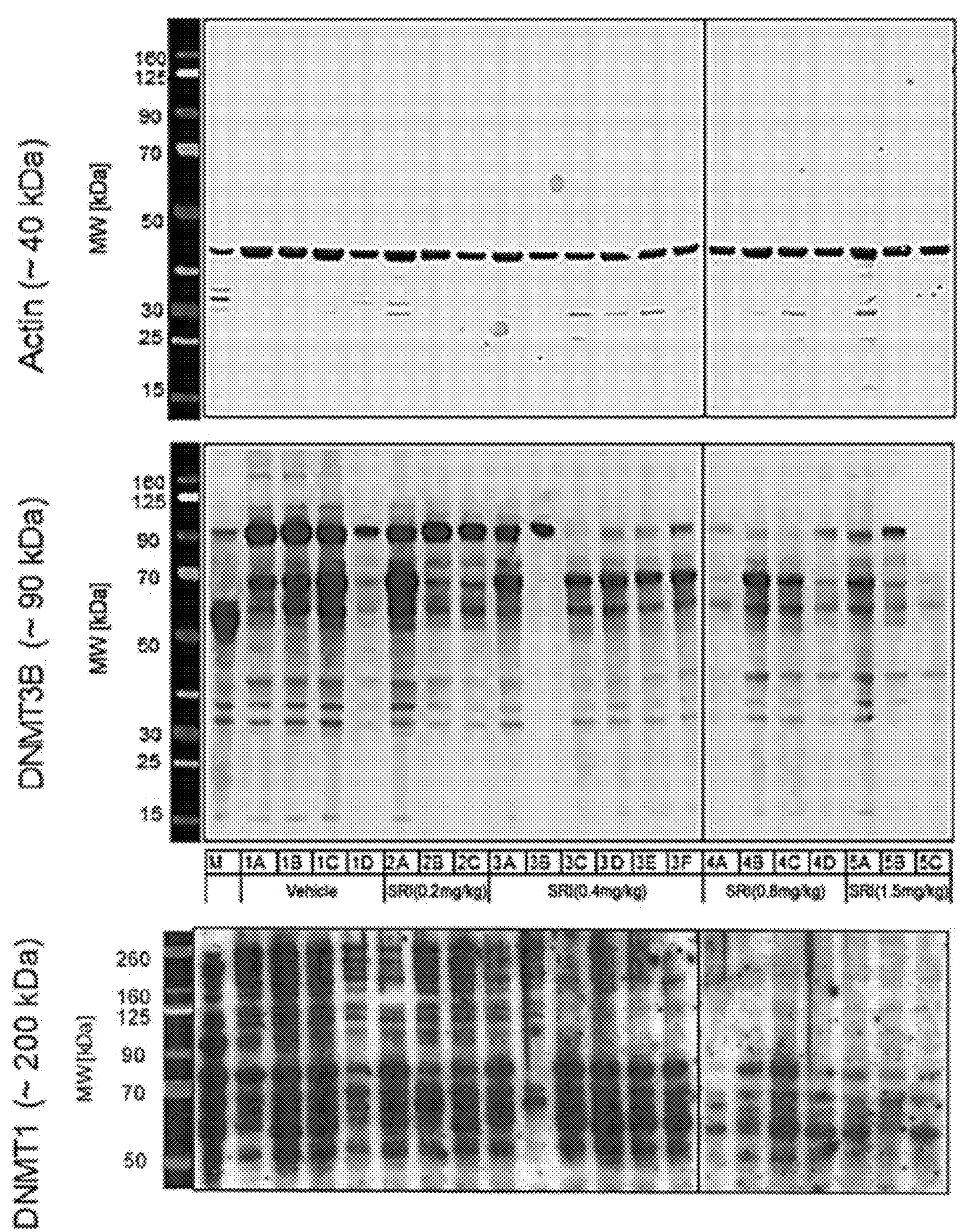
FIG. 26 shows the inhibition of DNMT3B expression in cancer tissues after treatment with NTX-301 in the Molm13 leukemia cell line xenograft model.

After Aza-T-dCyd administration, cancer tissues were harvested and analyzed by Western blotting (FIG. 26), and it was found that Aza-T-dCyd strongly inhibited DNMT1 and DNMT3B in a concentration-dependent manner, and this inhibition of DNMT3B is believed to contribute significantly to the potent anticancer effect of Aza-T-dCyd.

In the Molm13 AML xenograft model, the administration of Aza-T-dCyd showed strong anti-cancer efficacy through the inhibition of DNMT1 and simultaneous suppression of the expression of DNMT3B (a clear reduction of DNMT3B protein of approximately 90 kDa was observed upon treatment with Aza-T-dCyd at concentrations above 0.4 mg/kg).

After establishing a systemic MV4-11 engraftment model that more accurately depicts the disease in humans, Aza-T-dCyd was administered orally at doses ranging from 0.4 to 1.5 mg/kg. Aza-T-dCyd administration resulted in a statistically significant survival improvement at the lowest dose of 0.4 mg/kg. At the highest dose, more than half of the mice survived to the end of the experiment. Strong dose-dependent anti-cancer effects were observed at all doses without significant toxicity signals (body weight changes).

To confirm the superiority of Aza-T-dCyd over competing drugs, we performed experiments in the MV4-11 systemic AML model 5 to confirm that Aza-T-dCyd exhibits superior efficacy in a dose-dependent manner. After establishment of the systemic MV4-11 engraftment model, Aza-T-dCyd was administered orally at doses of 1.5, 2.0, and 2.5 mg/kg (using the standard dose/dosing schedule used in preclinical trials for decitabine/azacytidine). Compared to decitabine, which showed no therapeutic effect, and azacytidine, which showed no inhibition of leukemia progression as measured by blood counts, Aza-T-dCyd demonstrated very good anti-AML activity and improved survival in all dose groups.

After establishing a systemic MV4-11 engraftment model, blood was collected at pre-treatment (Day 21) and mid-treatment (Day 36, 56, 77) in the Aza-T-dCyd and Decitabine/Azacytidine groups and analyzed for complete blood count (CBC) values. In the Aza-T-dCyd group, we found that there were no changes in the following key parameters: white blood cells (WBC), red blood cells (RBC), neutrophils (Neutrophil), and platelets (Platelet). However, in the Decitabine group, all individuals died before blood samples were collected, and in the Azacytidine group, severe neutropenia was observed.

To determine whether the anti-cancer efficacy in the systemic MV4-11 engraftment model was directly related to the ability to suppress the number of cancer cells, we performed experiments to measure body luminescence after systemic engraftment using the luciferase-transfected Mv4-11 cell line. We found that the Aza-T-dCyd treatment inhibited body luminescence more strongly than the actual Azacytidine treatment. In the HL-60 AML xenograft model, NTX-301 (Aza-T-dCyd) at 2.0 mg/kg showed strong tumor suppression, while the maximum dose of decitabine at 0.75 mg/kg (animals died above this dose and could not be tested) showed no tumor suppression.

Figure 27:
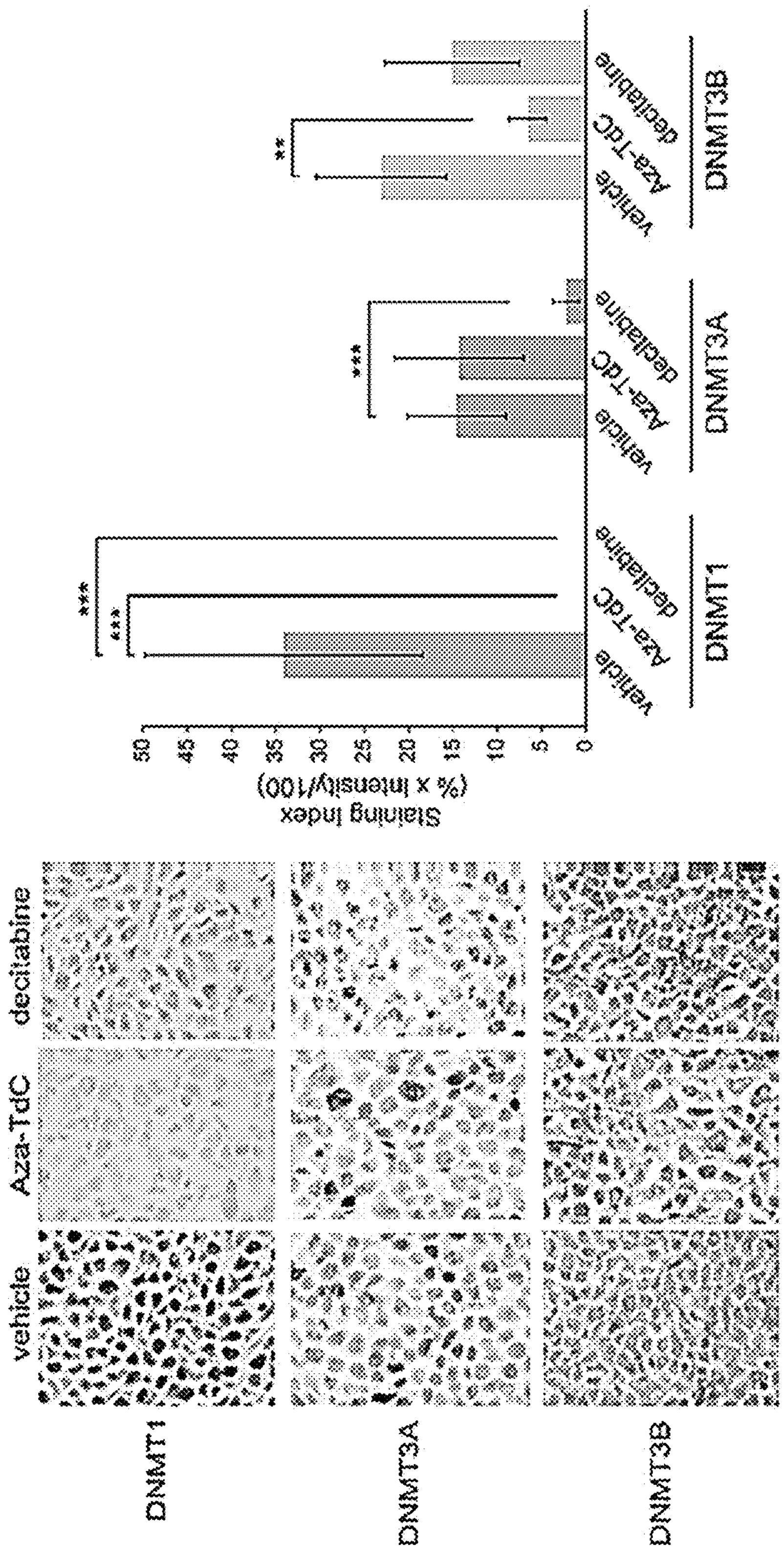
FIG. 27 shows the results of DNMT1, DNMT3A, and DNMT3B changes after treatment of HL-60 leukemia cell line xenograft model with Aza-T-dCyd and Decitabine.

As the efficacy of DNMT1 inhibitors correlates with their selective profile for targeting DNMT1 and the de novo methyltransferases DNMT3A and DNMT3B, we confirmed the expression of DNMT1, DNMT3A, and DNMT3B in the Aza-T-dCyd and Decitabine treated groups in this xenograft model (FIG. 27).

In the HL-60 xenograft mice model, 2 mg/kg of NTX-301 (Aza-T-dCyd) or 0.75 mg/kg of Decitabine were administered intraperitoneally, and then tumor samples were collected on day 11 to determine the expression of DNMT1, DNMT3A, and DNMT3B. DNMT1 expression was significantly reduced in both Aza-T-dCyd and Decitabine treated groups. On the other hand, the expression levels of DNMT3A and DNMT3B were different in the Aza-T-dCyd and Decitabine treatment groups. DNMT3A expression level was not affected by Aza-T-dCyd, and DNMT3B expression level was significantly reduced by Aza-T-dCyd, but no effect was observed by Deictabine.

It has been reported that high DNMT3B expression is associated with poor prognosis in AML, suggesting that the inhibition of DNMT3B by Aza-T-dCyd may be responsible for the superior anti-cancer effect of NTX-301 in the leukemia model.

4-2. T-ALL

To determine the efficacy of Aza-T-dCyd in another indication, T-ALL, we evaluated the efficacy of Aza-T-dCyd in a patient-derived ALL animal model.

Aza-T-dCyd was administered at doses of 0.5, 1, 1.5, and 2 mg/kg in ALL-Patient Derived Xenografts (PDX), with T-dCyd (DNMT1 inhibitor) used as a comparative control. Aza-T-dCyd was highly effective in pediatric ALL PDX at doses tolerated up to 1.5 mg/kg and was also effective in T-ALL, including ETP, a subtype of ALL with high unmet needs. In particular, it was found to induce robust tumor regression at lower doses compared to those in AML and to be able to maintain this remission for a longer period of time, suggesting its potential as a future treatment for ALL.

4-3. Various Solid Tumors

Unlike other DNMT1 inhibitors, Aza-T-dCyd has demonstrated significant efficacy in a variety of solid tumor animal models. In animal models of colorectal, bladder, ovarian, and lung cancer, Aza-T-dCyd showed excellent efficacy as shown in Table 7 (Cell line, animal, dose, and duration of treatment in solid cancer animal models).

TABLE 7

| Xenograft model | Mouse strain | NTX-301 (Aza-T-dCyd) Dose, (cycles) | Optimal T/C (%) (test/control) |
|---|---|---|---|
| HCT-116 (colorectal) | nude | 1 mg/kg, (4) | 21 |
| NCI-H522 (NSCLC) | nude | 2 mg/kg, (6) | 31 |
| OVCAR-3 (ovarian) | NSG | 0.5 mg/kg, (4) | 40 |
| | | 1 mg/kg, (4) | 4 |

TABLE 7-continued

| Xenograft model | Mouse strain | NTX-301 (Aza-T-dCyd) Dose, (cycles) | Optimal T/C (%) (test/control) |
|---|---|---|---|
| BL0382PD PDX (bladder) | NSG | 1 mg/kg, (4) | 23 |

The efficacy of Aza-T-dCyd was confirmed by tumor growth curves after administration of Aza-T-dCyd in various solid cancer xenograft models. Aza-T-dCyd at a dose of 1~2 mg/kg was administered repeatedly for 2~6 cycles in QD×5, showing excellent anti-cancer effects (evidenced by test/control (T/C) value≤40%).

In a colorectal (HCT-116) xenograft model, tumor growth inhibition was observed in the group treated with Aza-T-dCyd, with an optimal T/C of 21%. In contrast, Decitabine was not significantly effective with a T/C of 45%.

In the Non-Small Cell Lung cancer (NCI-H522) xenograft model, tumor growth inhibition was observed after treatment with Aza-T-dCyd, with an optimal T/C of 31%.

In the Ovarian (OVCAR-3) xenograft model, tumor regression was observed in the group treated with Aza-T-dCyd at a dose of 1 mg/kg, with an optimal T/C of 4%. The dose-dependent effect was confirmed by a T/C value of 40% at a dose of 0.5 mg/kg.

In the Bladder Tumor (BL0382PD PDX) xenograft model, tumor regression was observed in the group treated with NTX-301 at a dose of 1 mg/kg, with an optimal T/C of 23%. Decitabine showed toxicity after 2 cycles in the 0.75 mg/kg dose group.

Example 5: Safety (GLP-Toxicity)

As a preliminary toxicity assessment of the Aza-T-dCyd compound, preliminary toxicity experiments were conducted to determine the presence of toxicity symptoms (tissue changes) and DNA damage in bone marrow in mice after 2 weeks of systemic administration, and to assess the cellular composition in bone marrow of mice after 4 weeks of systemic administration.

In the Comet assay, weight changes by Aza-T-dCyd dose group were measured, and no significant weight changes were observed during the two-week systemic administration period, and no organ damage was seen at necropsy after two weeks.

Furthermore, when bone marrow was collected after two weeks of treatment and subjected to the Comet assay for DNA damage, there were no changes in various indicators of DNA damage compared to the untreated control group.

The cellular composition of the bone marrow of mice was evaluated after 4 weeks of continuous administration, and the results showed no changes in the various cells that make up the bone marrow, confirming that Aza-T-dCyd does not significantly affect the hematopoietic capacity in normal animals.

Aza-T-dCyd (NTX-301) has been tested in GLP toxicity studies and has a very good safety profile and wide therapeutic window in animal studies.

Aza-T-dCyd was found to be safe enough to achieve therapeutic concentrations in the above toxicity studies, with AUC values in the safe range.

In the MDS/AML model, the AUC value of Aza-T-dCyd shows efficacy at 60 h*ng/ml and the best therapeutic efficacy at 200-250 h*ng/ml, which is about 50% of the NOAEL value and about 25% of the HNSTD in the most sensitive species, indicating that Aza-T-dCyd has a very wide therapeutic window.

In other animal models, including other solid tumors and ALL, Aza-T-dCyd has shown excellent therapeutic efficacy at lower AUC exposures.

GLP-Tox studies have been conducted in rats and dogs, with 2 cycles of QD×5d at PO.

In the GLP rat Toxicology study, rats received 2.5, 5, and 10 mg/kg of Aza-T-dCyd (15, 30, and 60 mg/m2) per day. Toxicity target organs included bone marrow, thymus, heart, and testes. Testicular toxicity, including decreased sperm count, was reversible upon discontinuation, and the maximum tolerated dose (MTD) was >10 mg/kg per day (>60 $mg/m^2$).

In a GLP dog toxicology study, Aza-T-dCyd was administered at 0.15, 0.5, and 1.0 mg/kg (3, 10, and 20 $mg/m^2$) per day. The target organs were bone marrow, thymus, gastrointestinal tract, tonsils, and testes. The maximum tolerated dose (MTD) was between 0.5 and 1 mg/kg (10~20 $mg/m^2$) per day, the highest non-toxic dose (HNSTD) was 0.5 mg/kg (10 $mg/m^2$) per day, and the no observed adverse effect level (NOAEL) was <0.15 mg/kg (3) $mg/m^2$) per day.

Example 6: Combination Therapy with Aza-T-dCyd and Venetoclax

Recently, the standard regimen of AML treatment has been changing from decitabine/azacytidine alone to combining these drugs with the BCL-2 inhibitor Venetoclax. Therefore, we established an animal model of AML disease using the MV4-11 cell line and evaluated the drug effects of the combination of these drugs and the in vivo drug effects of the combination of Aza-T-dCyd and venetoclax.

6-1. NTX-301 Mouse Effective Dose

One of the major metabolic pathways of 5-azacytidine derivatives is deamination mediated by cytidine deaminase (CDA), which can inactivate Aza-T-dCyd (NTX-301).

The human dose of NTX-301 should be divided by 3 or 4 to adjust the mouse exposure.

In a human PK simulation study, the effective human dose of NTX-301 single agent was calculated to be 96 mg/day, based on an AUC value of 369 ng*h/mL at a dose of 2.0 mg/kg in mice. The 96 mg/day must be divided by 3 or 4, resulting in 24 to 32 mg/day.

For reference, the AUC value of the 16 mg/day dose in the NCI's Phase 1 trial was about 50 ng*h/mL, and converting this to the mouse AUC value (by a factor of 3-4) is 150-200 ng*h/mL. This was a safe and effective dose in mice.

Furthermore, based on the results of the combination with Venetoclax in the mouse model, an effective dose of 0.5 to 1.0 mg/kg was determined, which translates to a human dose of 8 to 16 mg+Venetoclax.

6-2. Mice

Female NCG mice (NOD-Prkdcem26Cd52112rgem26Cd22/NjuCrl, Charles River) were 9 weeks old on study day 1 and ranged from 19.8 to 25.3 g body weight (BW) on study day 1. Animals were fed ad libitum water (reverse osmosis, 1 ppm Cl) and NIH 31 Modified and Irradiated Lab Diet® consisting of 18.0% crude protein, 5.0% crude fat, and 5.0% crude fiber. Mice were housed in irradiated Enrich-o' Cobs™ laboratory animal bedding in static microisolators at 20-22° C. (68-72° F.) and 40-60% humidity with a 12-hour light cycle. The recommendations of the Guide for the Care and Use of Laboratory Animals were followed with respect to restraint, housing, surgical procedures, feeding and hydration, and veterinary care. The animal care and use program is accredited by the International Association for the Care and Use of Laboratory Animals (AAALAC), which ensures compliance with standards for the care and use of laboratory animals.

6-3. Tumor Cell Culture

The MV-4-11 human dual phenotype B-myelomonocytic leukemia cell line was obtained from the American Type Culture Collection (ATCC® CRL-9591™) and maintained in suspension culture in Iscove's Modified Dulbecco's Medium containing 100 units/mL penicillin G sodium salt, 100 μg/mL streptomycin sulfate, and 25 g/mL gentamicin.

The medium was supplemented with 10% fetal bovine serum and 2 mM glutamine. Leukemia cells were cultured in tissue culture flasks in a humidified incubator at 37° C. in an atmosphere of 5% $CO_2$ and 95% air.

6-4. In Vivo Transplantation

On the day of transplantation, MV411 cells were harvested during exponential growth and resuspended in phosphate-buffered saline (PBS). Each mouse was injected intravenously (i.v.) with $1\times10^7$ cells (0.2 mL suspension) in the tail vein.

Fourteen days after tumor cell implantation, designated as study day 1, animals were randomized into seven groups (n=8) based on body weight, with an average body weight of 21.9-22.9 g.

6-5. Therapeutic Preparation

Preparations were stored at −20° C. protected from light prior to formulation.

On each dosing day, Aza-T-dCyd (NTX-301) dosing solutions were prepared. Specifically, the required amount of compound was mixed with N-methyl-2-pyrrolidone (NMP) while vortexing, followed by polyethylene glycol (PEG) 400 and sonicated to obtain a clear solution. Saline was then added and further vortexed and sonicated to obtain a clear solution of 20% NMP/40% PEG400/40% saline. When administered at 10 mL/kg (0.2 mL/20 g animal), adjusted for the weight of each animal, the resulting 0.05, 0.1, 0.15 or 0.2 mg/mL dosage solution provides a dose of 0.5, 1, 1.5 or 2 mg/kg, respectively.

Venetoclax (ABT-199) and azacitidine (VIDAZA) were purchased. Venetoclax powder was freshly formulated in phosal 50 propylene glycol (PG) followed by PEG 400 and ethanol for each dose. The resulting 10 mg/mL dosing solution in 60% Phosal 50 PG/30% PEG 400/10% EtOH was adjusted for individual body weight when administered at a dosing volume of 10 mL/kg (0.200 mL/20 g mouse). On each dosing day, azacitidine powder was dissolved in PBS to obtain a 0.25 mg/mL dosing solution that delivers 2.5 mg/kg when administered in a dosing volume of 10 ml/kg (0.200 ml/20 g mouse), adjusted for each animal's body weight.

6-6. Treatment.

Figure 28:
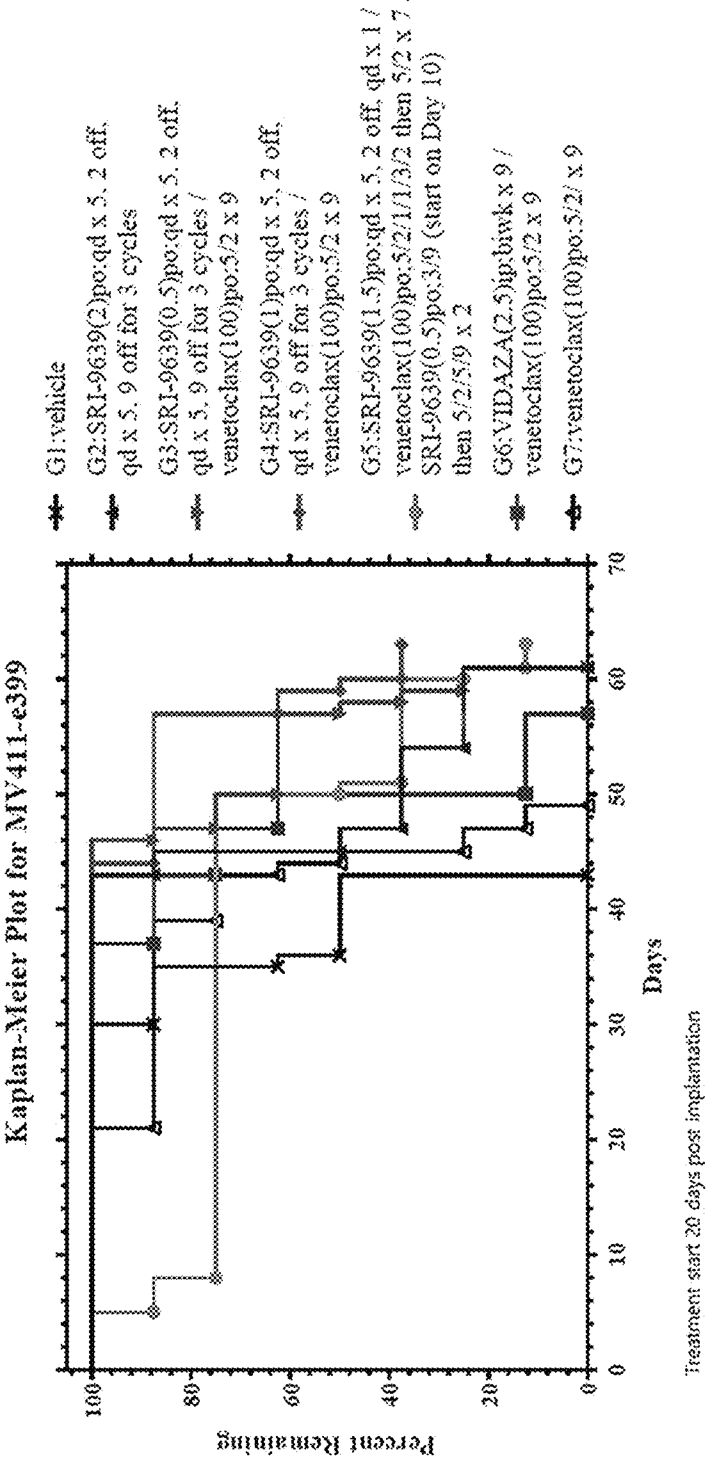
FIGS. 28 and 29 are CRL results showing the efficacy of NTX-301 (0.5, 1, 1.5 mg/kg) in combination with Venetoclax (100 mg/kg) in the MV4-11 AML cell line xenograft model.
Figure 29:
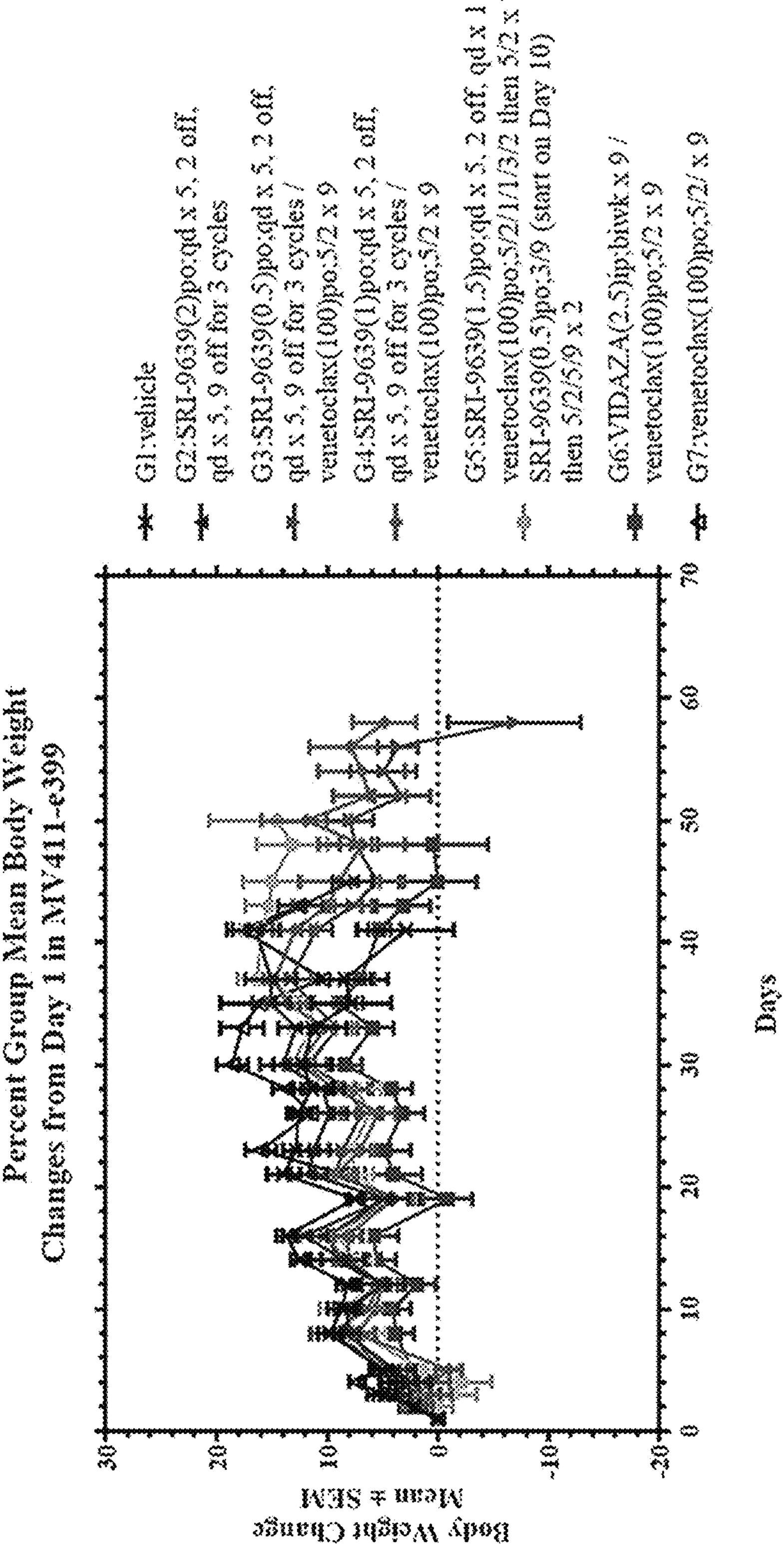

As a preceding experimental design, venetoclax was administered at a dose of 100 mg/kg, the dose and dosing schedule were as follows, and the treatment results are shown in FIGS. 28 and 29.

Treatment with vehicle (20% NMP/40% PEG400/40% saline), Aza-T-dCyd (NTX-301) or venetoclax was administered orally (p.o.) and treatment with azacitidine was administered intraperitoneally (i.p.). All preparations were administered at a volume of 10 mL/kg (0.2 mL/20 g mice) in proportion to the body weight of each animal.

Group 1 served as the control group and received 3 cycles of treatment: once daily for 5 days, followed by 2 days off, then once daily for 5 days, followed by 9 days off (qd×5, 2 off, qd×5, 9 off—3cycles).

Group 2 received 2 mg/kg Aza-T-dCyd (NTX-301) (qd×5, 2 off, qd×5, 9 off—3cycles).

Group 3 received 0.5 mg/kg Aza-T-dCyd (NTX-301) (qd×5, 2 off, qd×5, 9 off—3 cycles) in combination with 100 mg/kg Venetoclax (9 cycles, 5/2×9, once daily for 5 days, followed by 2 days off).

Group 4 received 1 mg/kg Aza-T-dCyd (NTX-301) (qd×5, 2 off, qd×5, 9 off—3 cycles) in combination with 100 mg/kg Venetoclax (5/2×9).

Group 5 was set to receive 1.5 mg/kg Aza-T-dCyd (NTX-301) (qd×5, 2 off, qd×5, 9 off—3 cycles) in combination with 100 mg/kg Venetoclax (5/2×9). Two mice in this group had treatment-related (TR) deaths, so treatment was stopped on day 8 and resumed on day 10 with 0.5 mg/kg Aza-T-dCyd (NTX-301) and 100 mg/kg Venetoclax.

Group 6 received 2.5 mg/kg azacitidine twice weekly for 8 consecutive weeks (biwk×8) with 100 mg/kg Venetoclax (5/2×9).

Group 7 received 100 mg/kg Venetoclax (5/2×9).

The results of the co-administration of venetoclax at a ½ lower dose of 50 mg/kg are shown in FIGS. 30 and 31, 32, and 33.

At this time, mice were categorized into seven groups (n=8) on day 1 of the study. The actual treatment regimens are summarized in Table 8.

TABLE 8

| Drugs and Treatment: | | | | | |
|---|---|---|---|---|---|
| Gr. | N | Agent | Formulation dose | Route | Schedule |
| 1# | 8 | vehicle | | po | qdx5, 2 off, qdx5, 9 off for 3 cycles |
| 2 | 8 | FFT1 | 2 mg/kg | po | qdx5, 2 off, qdx5, 9 off for 3 cycles |
| 3 | 8 | FFT1// | 0.5 mg/kg// | po// | qdx5, 2 off, qdx5, 9 off for 3 cycles// |
| | | venetoclax | 100 mg/kg | po | 5/2 × 9 |
| 4 | 8 | FFT1// | 1 mg/kg// | po// | qdx5, 2 off, qdx5, 9 off for 3 cycles// |
| | | venetoclax | 100 mg/kg | po | 5/2 × 9 |
| 5 | 8 | FFT1// | 1.5 mg/kg// | po// | qdx5, 2 off, qdx1// |
| | | Venetoclax// | 100 mg/kg// | po// | 5/2/1/1/3/2 then 5/2 × 7// |
| | | FFT1 | 0.5 mg/kg | po | 5/9 (start on day 10) then 5/2/5/9 × 2 |
| 6 | 8 | Azacitidine | 2.5 mg/kg// | ip// | biw × 9// |
| | | venetoclax | 100 mg/kg | po | 5/2 × 9 |
| 7 | 8 | venetoclax | 100 mg/kg | po | 5/2 × 9 |

#Control Group

Biw: two times per week 6-7. Endpoint for Survival Study

Treatment outcomes were evaluated based on time to endpoint (TTE) and the corresponding increase/decrease in life span (ILS). Individual animals were euthanized at the endpoint of lethargy or at the endpoint when the last day of the study (day 63) was reached. Lethargic signs of tumor progression, including hind limb dysfunction, ocular protrusion, weight loss, or neurologic signs (protrusions, behavioral changes, etc.) required euthanasia and all deaths due to tumor progression were classified as death in the survival study (DSS). TTE (in days) was recorded for each mouse that died of disease or was euthanized due to extensive tumor progression.

The median TTE of treated mice was expressed as a percentage (% T/C) of the median TTE of control mice, and the increase in life span (ILS) was calculated as follows $$ILS = \%\ T/C - 100$$

Where T=median TTE treatment, C=median TTE control. Therefore, if T=C, ILS=0%.

(For reference, the National Cancer Institute threshold for anti-acute myeloid leukemia activity of an agent in the L1210 model is an ILS of 25%).

6-8. Toxicity

Animals were weighed on Days 1-5 and then three times weekly until study termination (Day 63). Animals were observed frequently for obvious signs of treatment-related (TR) adverse events, and any notable clinical observations were recorded. Individual BW was monitored per protocol, and any animal with a weight loss greater than 30% in one measurement or greater than 25% in three measurements was euthanized and considered a TR death. Group average BW loss was also monitored according to the CR Discovery Services protocol. Acceptable toxicity was defined as a group mean BW loss of less than 20% over the study period and one or less TR death out of 10 treated animals (10%). Dosing was discontinued in groups where mean BW loss exceeded acceptable limits. Dosing was resumed at a lower level and/or reduced frequency when group mean BW recovered to an acceptable level. Deaths were categorized as TR if they were attributable to treatment adverse events as evidenced by clinical signs and/or autopsy. The TR classification could also be assigned to deaths from unknown causes during the dosing period or within 14 days of the last dose. Deaths were classified as non-treatment related (NTR) if there was evidence that the death was not treatment related but related to the tumor model. NTR deaths were further classified as NTR (due to accident or human error), NTRm (due to tumor dissemination by infiltration or metastasis confirmed at autopsy), and NTRu (etiology unknown).

6-9. Results of Aza-T-dCyd (NTX-301) in Combination with Venetoclax

Tumor Volume

Figure 30:
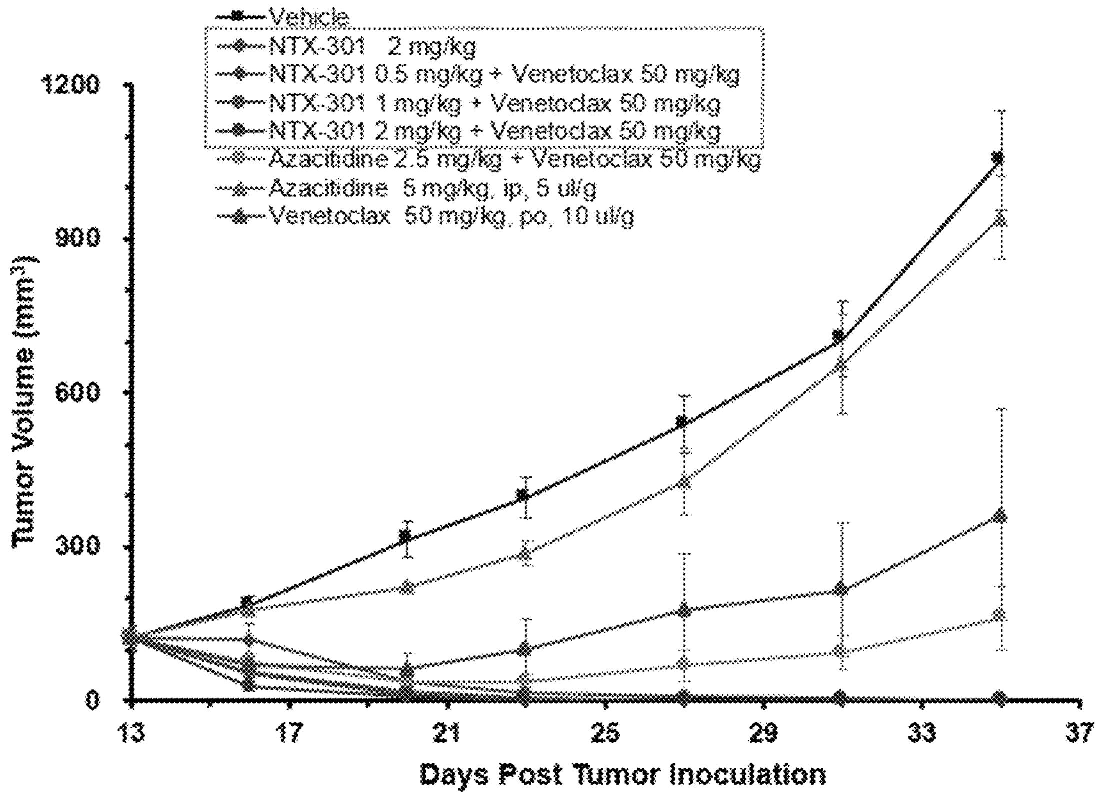
FIG. 30, FIG. 31, FIG. 32, and FIG. 33 are pharmaron results showing the efficacy of NTX-301 (0.5, 1, 2 mg/kg) in combination with Venetoclax (50 mg/kg) in the MV4-11 AML cell line xenograft model.
Figure 31:
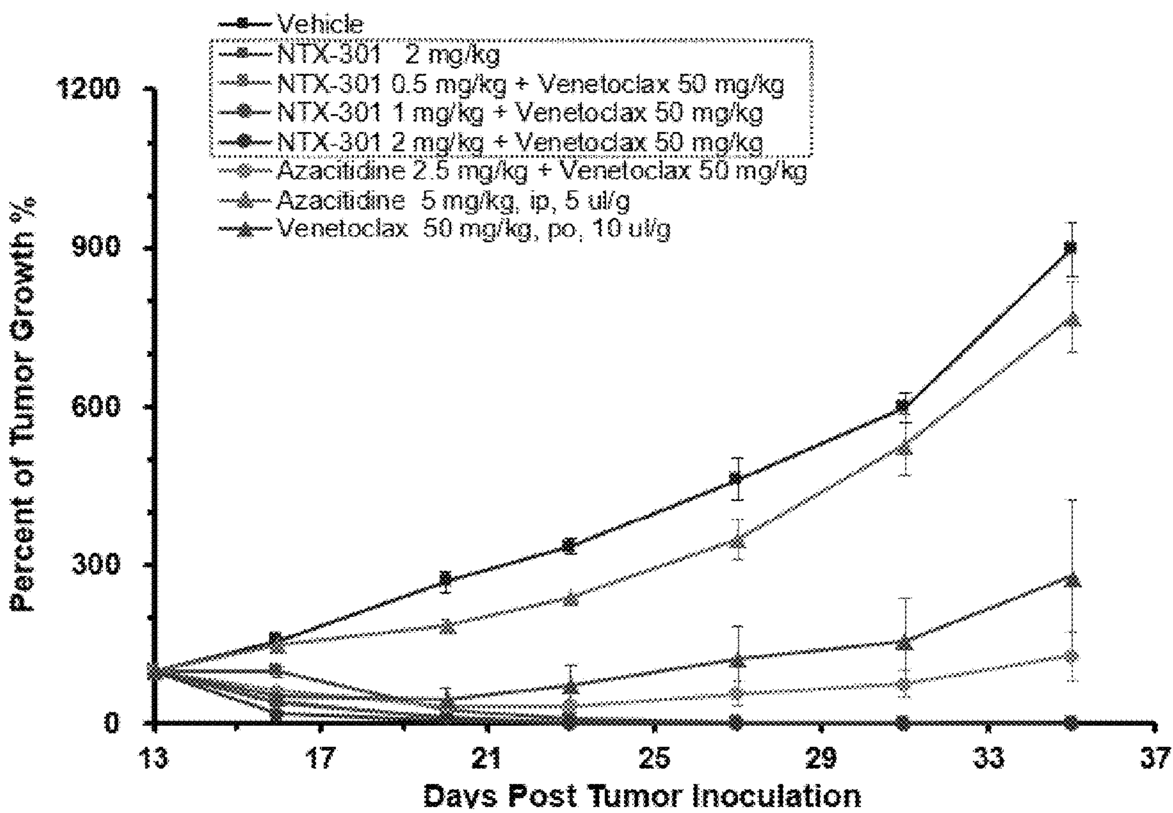
Figure 32:
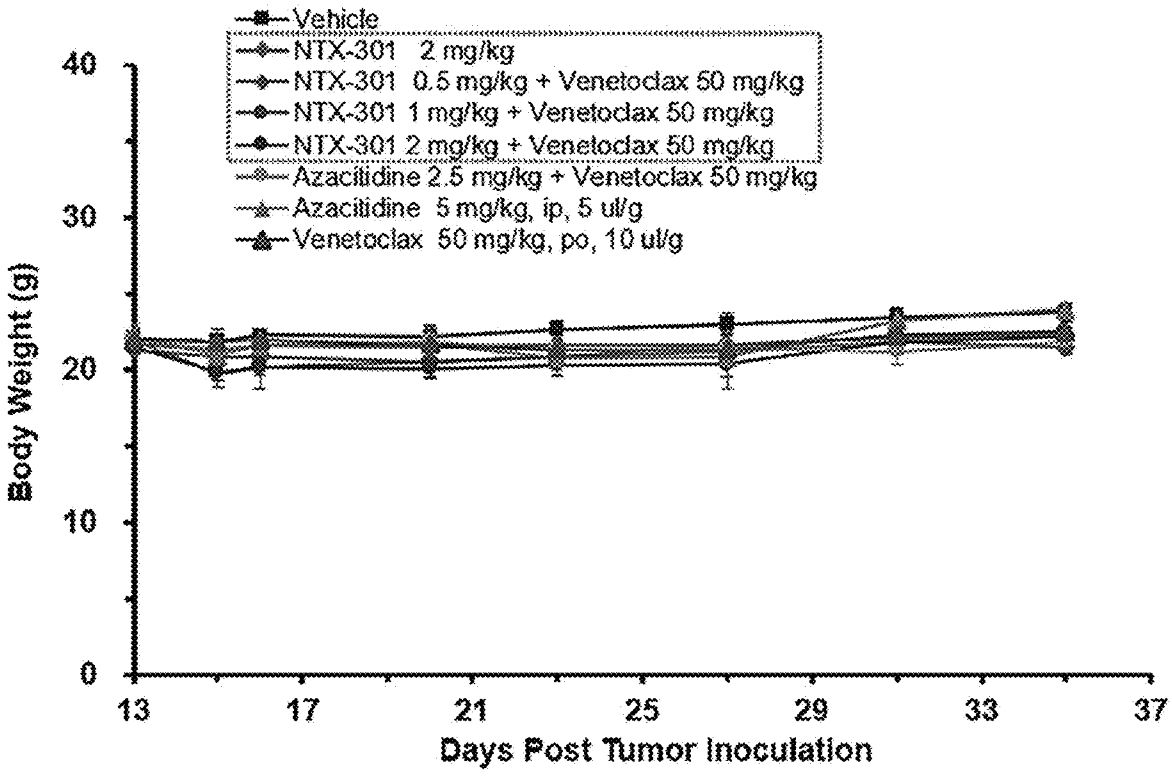
Figure 33:
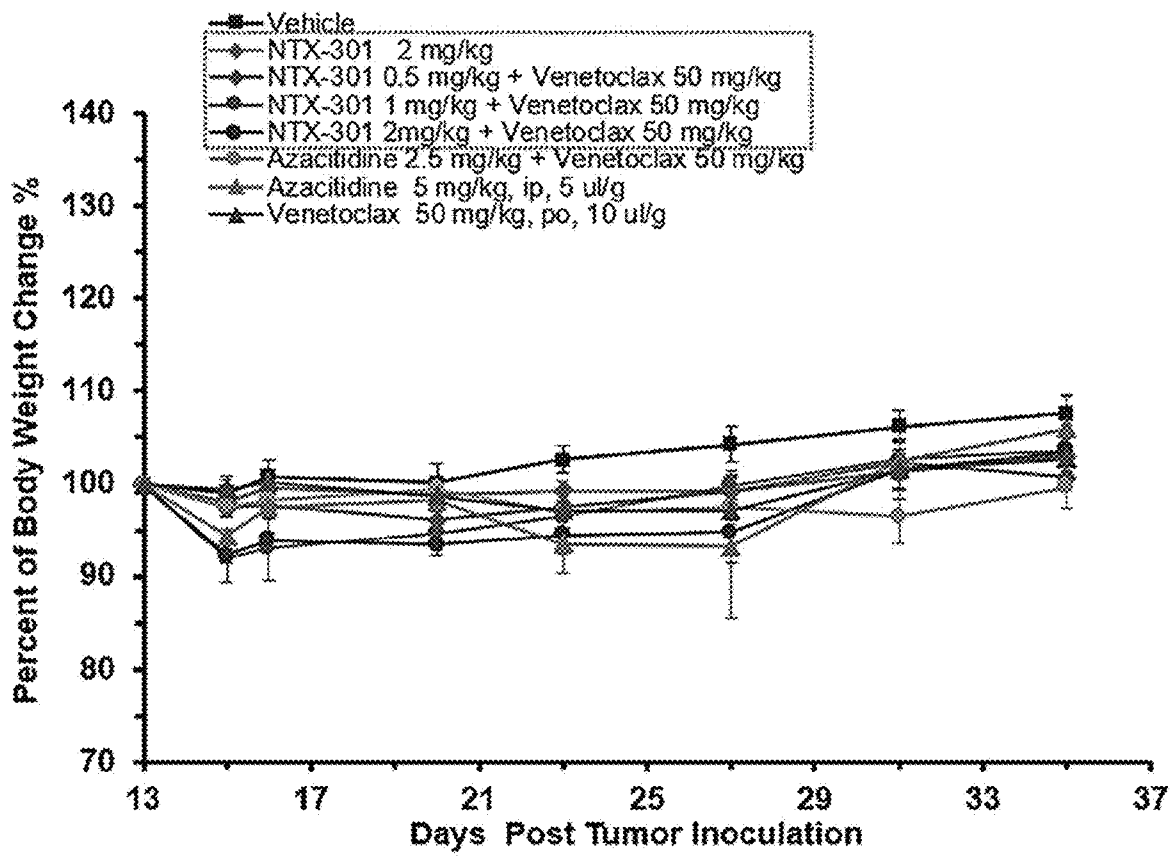

As shown in FIGS. 30 and 31, after establishing a xenograft AML model in n which MV4-11 AML cells were implanted subcutaneously in mice, the combination of venetoclax and Aza-T-dCyd at a dose of 0.5 mpk (15 mg) showed similarly good anti-cancer effects as Aza-T-dCyd at 2 mpk alone, compared to the failure of azacitidine alone to reduce tumor volume and the limited tumor regression seen with venetoclax alone.

In other words, it was confirmed that NTX-301 alone was sufficiently working, and when NTX-301 (0.5 mpk) and venetoclax were administered in combination, it was confirmed that there was an effect equivalent to single administration (complete tumor regression).

In FIG. 28 (MV4-11 Systemic model survival), when NTX-301 was co-administered with the standard dose of venetoclax (100 mg/kg), it was confirmed that a very low dose of NTX-301 was sufficient to achieve superior efficacy compared to competitive drugs.

Body Weight

After establishing a xenograft systemic AML model in which MV4-11 AML cells were implanted subcutaneously in mice, Aza-T-dCyd alone at 2.0 mpk for 1 cycle (5 days on, 2 days off, 5 days on, 9 days off) was administered (PO) or Aza-T-dCyd 0.5, 1.0 or 2.0 mpk plus venetoclax 50 mpk or 100 mpk administered orally (PO) for 1 cycle (venetoclax on for 5 days, off for 2 days, repeated for 3 weeks). Anti-cancer efficacy was determined in disease models in which azacitidine 5.0 mpk was administered intraperitoneally (IP) alone or in combination with optimal dose of azacitidine (2.5 mpk) and venetoclax 50 mpk or 100 mpk as a control.

As a result, as shown in FIG. 28, FIG. 29, FIG. 32 and FIG. 33, the survival rate was further improved in the group receiving venetoclax plus Aza-T-dCyd (0.5 mpk) than in the group receiving Azacitidine plus venetoclax or venetoclax alone, confirming the superior anti-cancer effect of venetoclax plus Aza-T-dCyd.

CONCLUSIONS

In a xenograft AML disease model using MV4-11 cell line implanted subcutaneously, NTX-301 alone was found to be sufficiently anti-tumorigenic, and the combination of NTX-301 and venetoclax was found to have equivalent pharmacological effects at a dose that was one-quarter lower than the dose administered alone.

Aza-T-dCyd 0.5 mpk also induced complete tumor regression, showing stronger cancer growth inhibition than the combination of Azacytidine and Venetoclax (FIG. 28).

As shown in FIG. 28, a 50% dose reduction from the MTD was required to combine decitabine/azacytidine with Venetoclax, and a dose reduction to 25% of the MTD resulted in a weakening of efficacy with good safety. In contrast, when NTX-301 was dosed at 25% of the MTD and co-administered with Venetoclax, the efficacy was significantly higher than that of the Azacytidine/Venetoclax group, suggesting that NTX-301 may have superior safety and efficacy in humans compared to the existing standard of care.

The invention claimed is:

1. A pharmaceutical composition for treating a solid tumor selected from the group consisting of colon cancer, bladder cancer, ovarian cancer, and lung cancer, or a hematologic cancer selected from the group consisting of MDS, AML, ALL, and CMML, comprising a 4'-thio-5-aza-2'-deoxycytidine drug and a venetoclax drug.

2. A kit for treating a solid tumor selected from the group consisting of colon cancer, bladder cancer, ovarian cancer, and lung cancer, or a hematologic cancer selected from the group consisting of MDS, AML, ALL, and CMML, comprising a 4'-thio-5-aza-2'-deoxycytidine drug and a venetoclax drug.

3. A method of treating a solid tumor selected from the group consisting of colon cancer, bladder cancer, ovarian cancer, and lung cancer, or a hematologic cancer selected from the group consisting of MDS, AML, ALL, and CMML, the method comprising administering to a subject in need thereof a 4'-thio-5-aza-2'-deoxycytidine drug and a venetoclax drug.

4. The method according to claim 3, wherein the 4'-thio-5-aza-2'-deoxycytidine drug and the venetoclax drug are co-administered in the same formulation or in different formulations.

5. The method according to claim 3, wherein the 4'-thio-5-aza-2'-deoxycytidine drug and the venetoclax drug are administered to the subject via the same route or different routes.

6. The method according to claim 3, wherein the 4'-thio-5-aza-2'-deoxycytidine drug and the venetoclax drug are administered to the subject as parenteral or oral administration.

7. The method according to claim 3, wherein the 4'-thio-5-aza-2'-deoxycytidine drug and the venetoclax drug are administered simultaneously or sequentially.

8. The method according to claim 3, wherein the 4'-thio-5-aza-2'-deoxycytidine drug is administered at 8 mg/day or more and less than 32 mg/day.

9. The method according to claim 3, the 4'-thio-5-aza-2'-deoxycytidine drug is administered at a dose of 25% to 75% of the maximum tolerated dose.

10. The method according to claim 3, wherein the 4'-thio-5-aza-2'-deoxycytidine drug reduces DNMT1 protein or inhibits DNMT1 in a concentration-dependent manner.

11. The method according to claim 3, wherein the 4'-thio-5-aza-2'-deoxycytidine drug is administered at a high dose that prevents the mechanisms of resistance development from overactivating base excision repair (BER), one of the methods of DNA damage repair.

12. The method according to claim 3, wherein the subject meets one or more of the following criteria:

(i) who has developed resistance to a DNMT1 inhibitor; who has accumulated altered epigenetic DNA methylation patterns in cancer cells relative to normal cells;

(ii) who has been informed of or diagnosed with a poor prognosis or potential for resistance to DNMT1 inhibitors; who has been diagnosed with an elevated level of lineage commitment master transcription factors selected from the group consisting of CEBP/alpha, Pu.1 and GATA factors, while expression of CEBP/epsilon or late developmental stage transcription factors remains low due to hypermethylation of each gene, relative to normal individuals;

(iii) who has a known or diagnosed risk of developing nucleoside metabolism resistance when receiving nucleoside-based anticancer agents;

(iv) who is a candidate for platinum-based anticancer agents; who have developed or are likely to develop resistance to platinum-based anticancer agents; and (v) who is epigenetically silenced for tumor suppressor genes and/or SLFN11 relative to normal individuals.

13. The method according to claim 3, wherein the drug 4'-thio-5-aza-2'-deoxycytidine is administered as a targeted anti-cancer agent at or above a standard dosage of a DNMT1 inhibitor to a patient in need thereof who is limited in the standard dosage of a DNMT1 inhibitor as a standard therapy due to the fact that the DNMT1 inhibitor damages, thereby damaging normal tissue as well as cancer cells.

14. The method according to claim 3, wherein the subject is:

a patient diagnosed with acute myeloid leukemia (AML), myelodysplastic syndrome (MDS), or acute lymphocytic leukemia (ALL), a patient with platinum-resistant recurrent end-stage ovarian cancer, a patient with platinum-resistant metastatic bladder cancer, a patient with metastatic bladder cancer, a patient with p53 mutated bladder cancer or hypermethylated SLFN11 bladder cancer, which are specific biomarkers to be treated, or a patient diagnosed with stage III or IV ovarian cancer.

15. The method according to claim 3, wherein the subject is:

a patient with chronic myelomonocytic leukemia (CML), a patient with T-cell acute lymphoblastic leukemia (T-ALL), a patient with chronic lymphocytic leukemia (CLL), a high-risk patient with genomic abnormalities, a patient with relapsed secondary AML (sAML), a patient with treatment-related AML (t-AML) due to prior therapy, or a drug-resistant/refractory patient.

* * * * *